United States Patent
Saulenas et al.

(10) Patent No.: US 12,245,830 B2
(45) Date of Patent: Mar. 11, 2025

(54) ARTICULABLE WRIST WITH FLEXIBLE MEMBER AND PIVOT GUIDES

(71) Applicant: Cilag GmbH International, Zug (CH)

(72) Inventors: William George Saulenas, Cincinnati, OH (US); Tyler N. Brehm, Dayton, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/462,741

(22) Filed: Sep. 7, 2023

(65) Prior Publication Data
US 2023/0414302 A1    Dec. 28, 2023

Related U.S. Application Data

(63) Continuation of application No. 16/547,217, filed on Aug. 21, 2019, now Pat. No. 11,771,507.

(51) Int. Cl.
*A61B 34/30* (2016.01)
*A61B 17/00* (2006.01)
(Continued)

(52) U.S. Cl.
CPC ........ *A61B 34/30* (2016.02); *A61B 17/00234* (2013.01); *A61B 17/2909* (2013.01);
(Continued)

(58) Field of Classification Search
CPC ............... A61B 17/2804; A61B 34/71; A61B 2017/2804; A61B 2017/2908;
(Continued)

(56) References Cited

U.S. PATENT DOCUMENTS

| | | | |
|---|---|---|---|
| 9,033,998 B1* | 5/2015 | Schaible | A61B 34/30 606/130 |
| 2008/0058861 A1* | 3/2008 | Cooper | A61B 34/70 606/205 |
| 2008/0177284 A1 | 7/2008 | Lee | |
| 2009/0112316 A1* | 4/2009 | Umemoto | A61B 34/71 700/258 |

(Continued)

FOREIGN PATENT DOCUMENTS

| | | |
|---|---|---|
| JP | 2000205328 A | 7/2000 |
| JP | 2006-034978 A | 2/2006 |

(Continued)

OTHER PUBLICATIONS

ISR-WO from corresponding PCT application PCT/IB2020/057691 mailed Nov. 9, 2020.

*Primary Examiner* — Martin T Ton
(74) *Attorney, Agent, or Firm* — Vorys, Sater, Seymour and Pease LLP

(57) ABSTRACT

An articulable wrist for an end effector includes a first linkage, a second linkage rotatably coupled to the first linkage at a first articulation joint, and a flexible member extending at least partially through a central channel cooperatively defined by the first and second linkages. A first pivot guide is rotatably coupled to the second linkage at the first articulation joint and rotatable about a first pivot axis extending through the first articulation joint, the first pivot guide defining a central aperture alignable with the central channel and sized to accommodate the flexible member therethrough. The first pivot guide supports an outer diameter of the flexible member at the first articulation joint and prevents the flexible member from flexing beyond the first pivot axis during articulation.

20 Claims, 15 Drawing Sheets

(51) Int. Cl.
*A61B 17/29* (2006.01)
*A61B 34/00* (2016.01)

(52) U.S. Cl.
CPC .... *A61B 34/71* (2016.02); *A61B 2017/00477* (2013.01); *A61B 2017/2926* (2013.01); *A61B 2034/301* (2016.02); *A61B 2034/305* (2016.02); *A61B 2034/715* (2016.02)

(58) Field of Classification Search
CPC .... A61B 2017/2926; A61B 2017/2933; A61B 2017/2934; A61B 2017/2936; A61B 2017/2937; A61B 2017/2939; A61B 2017/2944; A61B 2017/2947; A61B 2034/301; A61B 2034/305; A61B 2034/306
See application file for complete search history.

(56) References Cited

U.S. PATENT DOCUMENTS

| | | | |
|---|---|---|---|
| 2011/0028991 A1* | 2/2011 | Ikeda | A61B 34/71 606/130 |
| 2017/0095922 A1* | 4/2017 | Licht | A61B 34/71 |
| 2018/0078322 A1* | 3/2018 | Haraguchi | A61B 34/71 |
| 2018/0206904 A1 | 7/2018 | Felder | |
| 2020/0315722 A1* | 10/2020 | Penny | A61B 90/08 |

FOREIGN PATENT DOCUMENTS

| | | |
|---|---|---|
| JP | 2008511404 A | 4/2008 |
| JP | 2009136684 A | 6/2009 |
| JP | 2018531694 A | 11/2018 |

* cited by examiner

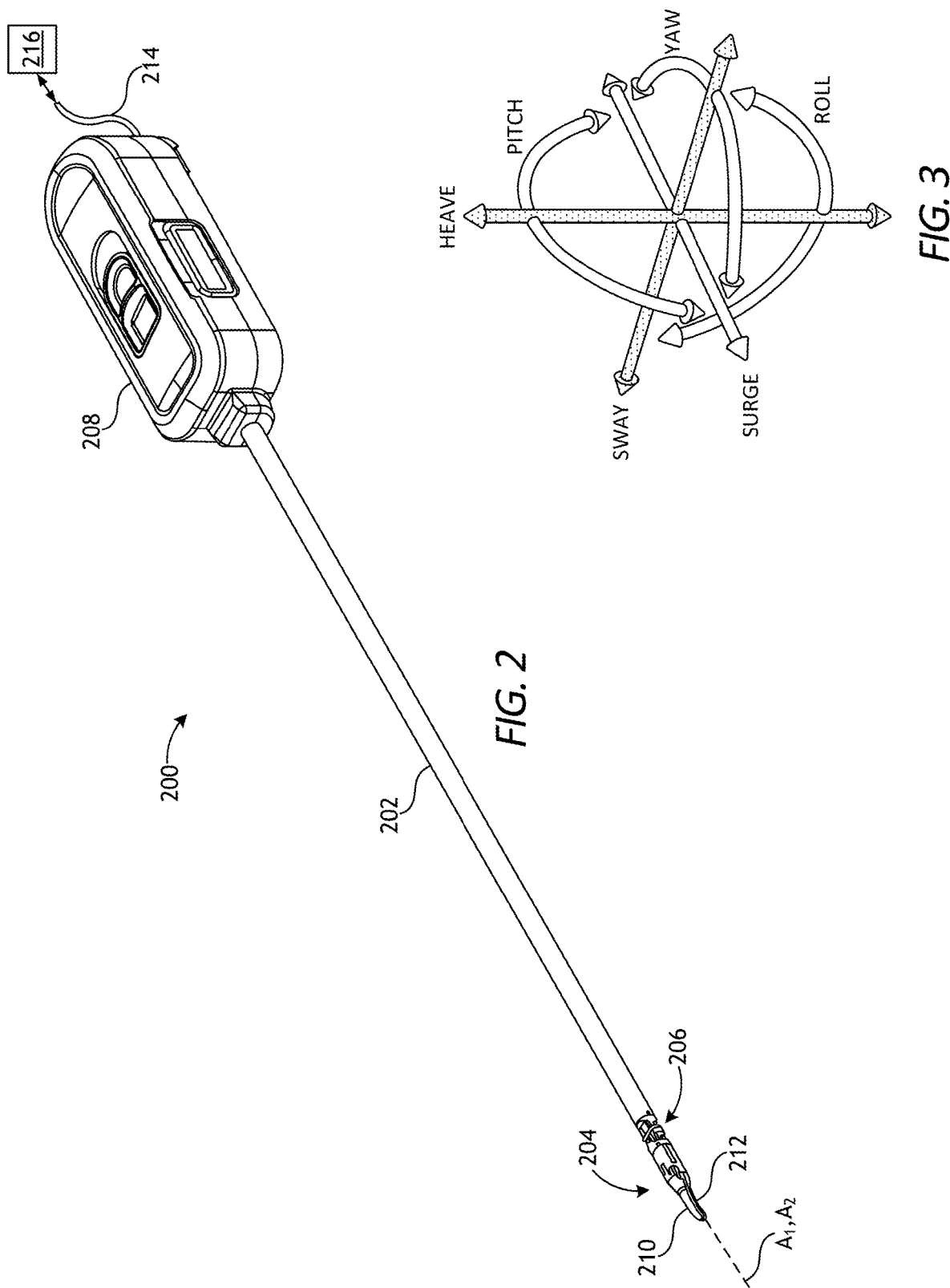

ARTICULABLE WRIST WITH FLEXIBLE MEMBER AND PIVOT GUIDES

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Various robotic systems have recently been developed to assist in MIS procedures. Robotic systems can allow for more instinctive hand movements by maintaining natural eye-hand axis. Robotic systems can also allow for more degrees of freedom in movement by including an articulable "wrist" joint that creates a more natural hand-like articulation. In such systems, an end effector positioned at the distal end of the instrument can be articulated (moved) using a cable driven motion system having one or more drive cables (or other elongate members) that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system and thereby actively controlling the tension balance in the drive cables. Moving the drive cables articulates the end effector to desired angular positions and configurations.

In articulated robotic tools, cables that actuate jaw opening, closing, and clamping are routed through the wrist and articulation joints to reach the end effector. To help guide the position of the cables through the pitch and yaw articulation joints of the wrist, the cables can be further routed through a flexible member that also extends through the wrist. The flexible member is often referred to as a "multilumen" since it defines a plurality of axially-extending cable pathways or conduits that accommodate the various cables.

The cables extending through the flexible member and articulation joints of the wrist are not typically constrained to be on the centerline axis at the articulation pivots. Consequently, as the articulation joint angle moves away from the straight position during actuation, the cable pathways through the flexible member can dip above or below the pivot axis governed by the stiffness of the flexible member and its ability to flex in response to the clamping load. As cables tighten under tensile loading, such as when a high closure force is applied to a closure cable to "clamp" the jaws on tissue, they will tend to find the shortest path through the articulation pivots, which may cause the cables to dip below the pivot axis. If a cable dips below the pivot axis, this can create an unbalanced moment that causes the jaws to move abruptly (i.e., dive) in the direction of the imbalance. This unexpected tip deflection or "tip dive" is undesirable in surgical use where the jaws are clamping critical structures.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIG. 2 is an isometric side view of an example surgical tool that may incorporate some or all of the principles of the present disclosure.

FIG. 3 illustrates potential degrees of freedom in which the wrist of the surgical tool of FIG. 2 may be able to articulate (pivot) or translate.

DETAILED DESCRIPTION

Figure 1:
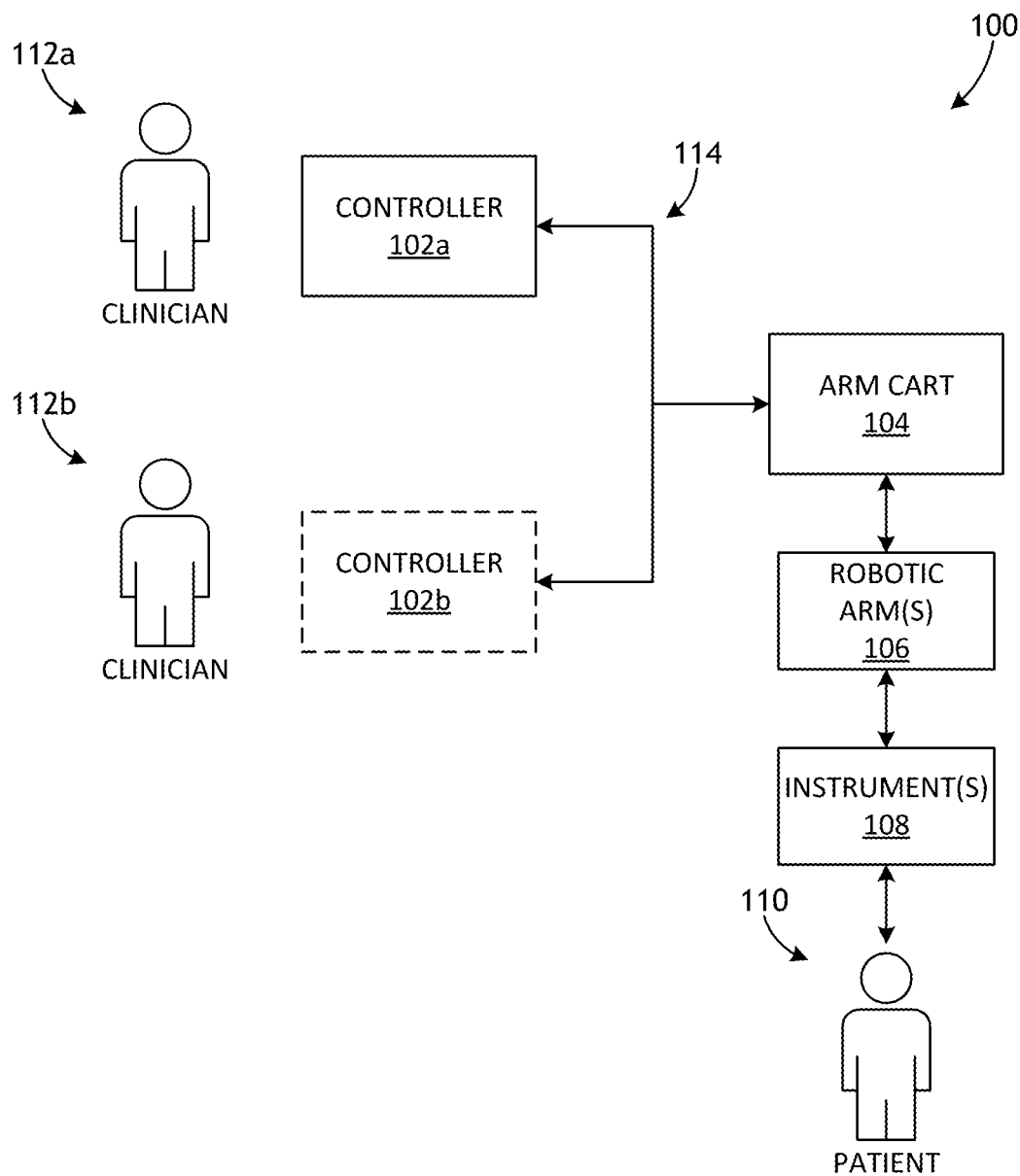
FIG. 1 is a block diagram of an example robotic surgical system that may incorporate some or all of the principles of the present disclosure.

The present disclosure is related to robotic surgical systems and, more particularly, to end effectors with articulable wrists that include a flexible member extending through the articulable wrists and sub-articulation pivot guides arranged at each articulation joint to help support the flexible member and prevent closure and open cables from migrating past corresponding pivot axes.

In cable articulated robotic tools, undesirable motion of the jaw tip can result when a high closure force is applied to "clamp" the jaw on tissue in a surgical procedure. This jaw tip motion is generated by slight off center positional offsets of the closure cable in the articulation joints at certain poses. This creates an unbalancing moment which caused the jaw to move abruptly (dive) in the direction of the imbalance. This "tip dive" is unexpected and undesirable in surgical use where the jaw is clamping critical structures. Simulation studies have shown that the end effector will move in the direction of articulation if the centerline of the closure cable falls below the articulation pivot axis due to flexure of an unsupported flexible member at the articulation joint.

Embodiments described herein disclose an articulable wrist for an end effector of a surgical tool. The articulable wrist includes a first linkage, a second linkage rotatably coupled to the first linkage at a first articulation joint, and a flexible member extending at least partially through a central channel cooperatively defined by the first and second linkages. A first pivot guide is rotatably coupled to the second linkage at the first articulation joint and rotatable about a first pivot axis extending through the first articulation joint, the first pivot guide defining a central aperture alignable with the central channel and sized to accommodate the flexible member therethrough. The first pivot guide supports an outer diameter of the flexible member at the first articulation joint and prevents the flexible member from flexing beyond the first pivot axis during articulation. In some embodiments, an axially-extending conduit is defined in the flexible member to receive a closure cable used to actuate jaws of the end effector. The pivot guide supports the outer diameter of the flexible member at the first articulation joint and prevents a centerline of the closure cable from deviating below the first pivot axis during clamping.

Accordingly, embodiments of the present disclosure employ sub-articulation pivot guides operable to contain the outer diameter of the flexible member and constrain its ability to flex beyond the pivoting axis. Consequently, the closure cable will not be able to deviate below the pivot axis during closure because it is captured by these pivot guides. This will reduce the offset moment created when tension on the closure cable is increased during jaw clamping. This constraint may also reduce the effect of undesirable end effector motion ("tip dive"). The pivot guides may pivot at an angle that bisects the overall articulation angles, and this will guide smooth angular transitions for the cables and wires contained within the flexible member. The pivot guides can be present in both the pitch and yaw articulation joints.

FIG. 1 is a block diagram of an example robotic surgical system 100 that may incorporate some or all of the principles of the present disclosure. As illustrated, the system 100 can include at least one set of user input controllers 102a and at least one control computer 104. The control computer 104 may be mechanically and/or electrically coupled to a robotic manipulator and, more particularly, to one or more robotic arms 106 (alternately referred to as "tool drivers"). In some embodiments, the robotic manipulator may be included in or otherwise mounted to an arm cart capable of making the system portable. Each robotic arm 106 may include and otherwise provide a location for mounting one or more surgical instruments or tools 108 for performing various surgical tasks on a patient 110. Operation of the robotic arms 106 and associated tools 108 may be directed by a clinician 112a (e.g., a surgeon) from the user input controller 102a.

In some embodiments, a second set of user input controllers 102b (shown in dashed lines) may be operated by a second clinician 112b to direct operation of the robotic arms 106 and tools 108 in conjunction with the first clinician 112a. In such embodiments, for example, each clinician 112a,b may control different robotic arms 106 or, in some cases, complete control of the robotic arms 106 may be passed between the clinicians 112a,b. In some embodiments, additional robotic manipulators (not shown) having additional robotic arms (not shown) may be utilized during surgery on the patient 110, and these additional robotic arms may be controlled by one or more of the user input controllers 102a,b.

The control computer 104 and the user input controllers 102a,b may be in communication with one another via a communications link 114, which may be any type of wired or wireless telecommunications means configured to carry a variety of communication signals (e.g., electrical, optical, infrared, etc.) and according to any communications protocol.

The user input controllers 102a,b generally include one or more physical controllers that can be grasped by the clinician 112a,b and manipulated in space while viewing the procedure via a stereo display. The physical controllers generally comprise manual input devices movable in multiple degrees of freedom, and often include an actuatable handle or pedal for actuating the surgical tool(s) 108. The control computer 104 can also include an optional feedback meter viewable by the clinician 112a,b via a display to provide a visual indication of various surgical instrument metrics, such as the amount of force being applied to the surgical instrument (i.e., a cutting instrument or dynamic clamping member).

FIG. 2 is an isometric side view of an example surgical tool 200 that may incorporate some or all of the principles of the present disclosure. The surgical tool 200 may be the same as or similar to the surgical tool(s) 108 of FIG. 1 and, therefore, may be used in conjunction with a robotic surgical system, such as the robotic surgical system 100 of FIG. 1. In other embodiments, however, aspects of the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint" or an "articulable wrist joint") that couples the end effector 204 to the distal end of the shaft 202, and a drive housing 208 coupled to the proximal end of the shaft 202. In robotic surgical systems, the drive housing 208 can include coupling features that releasably couple the surgical tool 200 to a robotic surgical system (e.g., the robotic arm 106 of FIG. 1).

The terms "proximal" and "distal" are defined herein relative to a robotic surgical system having an interface configured to mechanically and electrically couple the surgical tool 200 (e.g., the drive housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. To accomplish this, the drive housing 208 includes (contains) various drive inputs and mechanisms (e.g., gears, actuators, etc.) designed to control operation of various features associated with the end effector 204 (e.g., clamping, firing, rotation, articulation, cutting, etc.). In at least some applications, the shaft 202, and hence the end effector 204 coupled thereto, is configured to rotate about a longitudinal axis $A_1$ of the shaft 202. In such embodiments, at least one of the drive inputs controls rotational movement of the shaft 202 about the longitudinal axis $A_1$.

The surgical tool 200 may include, but is not limited to, forceps, a grasper, a needle driver, scissors, an electro cautery tool, a vessel sealer, a stapler, a clip applier, a hook, a spatula, a suction tool, an irrigation tool, an imaging device (e.g., an endoscope or ultrasonic probe), or any combination thereof. In some embodiments, the surgical tool 200 may be configured to apply energy to tissue, such as radio frequency (RF) energy. In the illustrated embodiment, the end effector 204 comprises a tissue grasper and vessel sealer that includes opposing jaws 210, 212 configured to move (articulate) between open and closed positions. As will be appreciated, however, the opposing jaws 210, 212 may alternatively form part of other types of end effectors such as, but not limited to, surgical scissors, a clip applier, a needle driver, a babcock including a pair of opposed grasping jaws, bipolar jaws (e.g., bipolar Maryland grasper, forceps, a fenestrated grasper, etc.), etc. One or both of the jaws 210, 212 may be configured to pivot relative to the other to open and close the jaws 210, 212. The principles of the present disclosure, however, are equally applicable to end effectors without opposing jaws.

FIG. 3 illustrates the potential degrees of freedom in which the wrist 206 may be able to articulate (pivot). The wrist 206 comprises a joint configured to allow pivoting movement of the end effector 204 relative to the shaft 202. The degrees of freedom of the wrist 206 are represented by three translational variables (i.e., surge, heave, and sway) and three rotational variables (i.e., Euler angles or roll, pitch, and yaw). The translational and rotational variables describe the position and orientation of the end effector 204 with respect to a given reference Cartesian frame. "Surge" refers to forward and backward translational movement, "heave" refers to translational movement up and down, and "sway" refers to translational movement left and right. "Roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system that facilitates movement and articulation of the end effector 204 relative to the shaft 202. Moving (actuating) the drive cables moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. In the articulated position, the longitudinal axes $A_1$, $A_2$ would be angularly offset from each other such that the end effector 204 is at a non-zero angle relative to the shaft 202.

In some embodiments, the surgical tool 200 may be supplied with electrical power (current) via a power cable 214 coupled to the drive housing 208. In other embodiments, the power cable 214 may be omitted and electrical power may be supplied to the surgical tool 200 via an internal power source, such as one or more batteries or fuel cells. In such embodiments, the surgical tool 200 may alternatively be characterized and otherwise referred to as an "electrosurgical instrument" capable of providing electrical energy to the end effector 204. The power cable 214 may place the surgical tool 200 in communication with a generator 216 that supplies energy, such as electrical energy (e.g., radio frequency energy), ultrasonic energy, microwave energy, heat energy, or any combination thereof, to the surgical tool 200 and, more particularly, to the end effector 204.

Figure 4:
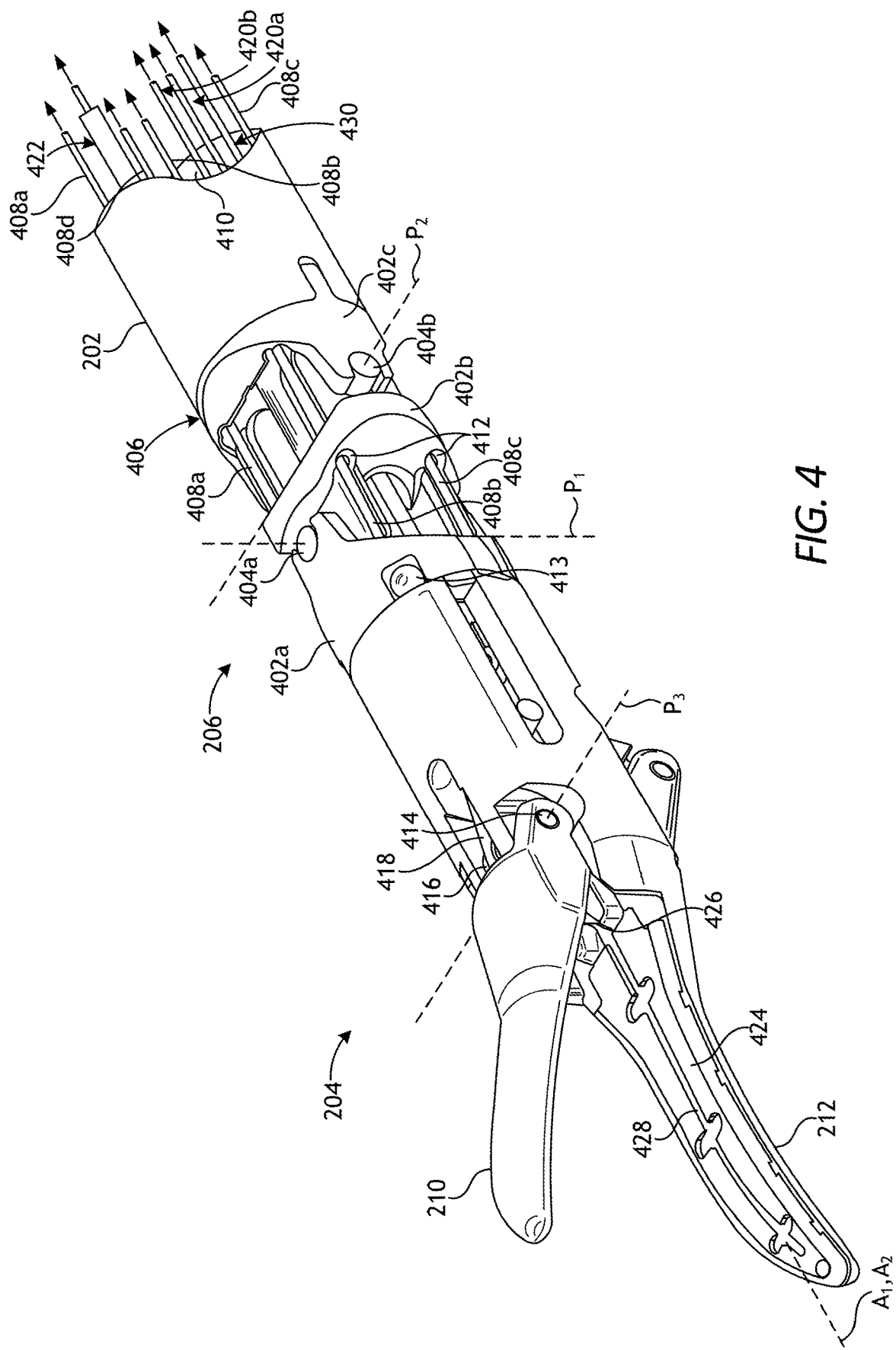
FIG. 4 is an enlarged isometric view of the distal end of the surgical tool of FIG. 2.

FIG. 4 is an enlarged isometric view of the distal end of the surgical tool 200 of FIG. 2. More specifically, FIG. 4 depicts an enlarged view of the end effector 204 and the wrist 206, with the jaws 210, 212 of the end effector 204 in the open position. The wrist 206 operatively couples the end effector 204 to the shaft 202. In some embodiments, however, a shaft adapter may be directly coupled to the wrist 206 and otherwise interpose the shaft 202 and the wrist 206. Accordingly, the wrist 206 may be operatively coupled to the shaft 202 either through a direct coupling engagement where the wrist 206 is directly coupled to the distal end of the shaft 202, or an indirect coupling engagement where a shaft adapter interposes the wrist 206 and the distal end of the shaft 202. As used herein, the term "operatively couple" refers to a direct or indirect coupling engagement between two components.

To operatively couple the end effector 204 to the shaft 202, the wrist 206 includes a first or "distal" linkage 402a, a second or "intermediate" linkage 402b, and a third or "proximal" linkage 402c. The linkages 402a-c facilitate articulation of the end effector 204 relative to the elongate shaft 202. Articulation via the linkages 402a-c may be limited to pitch only, yaw only, or a combination of pitch and yaw. As illustrated, the distal end of the distal linkage 402a may be coupled to the end effector 204 and, more particularly, to the lower jaw 212 (or an extension of the lower jaw 212). The proximal end of the distal linkage 402a may be rotatably coupled to the intermediate linkage 402b at a first axle 404a, and the intermediate linkage 402b may also be rotatably coupled to the proximal linkage 402c at a second axle 404b. The proximal end of the proximal linkage 402c may be coupled to a distal end 406 of the shaft 202 (or alternatively a shaft adapter).

A first pivot axis $P_1$ extends through the first axle 404a and a second pivot axis $P_2$ extends through the second axle 404b. The first pivot axis $P_1$ is substantially perpendicular (orthogonal) to the longitudinal axis $A_2$ of the end effector 204, and the second pivot axis $P_2$ is substantially perpendicular (orthogonal) to both the longitudinal axis $A_2$ and the first pivot axis $P_1$. Movement about the first pivot axis $P_1$ provides "yaw" articulation of the end effector 204, and movement about the second pivot axis $P_2$ provides "pitch" articulation of the end effector 204. Alternatively, the first pivot axis $P_1$ could be configured to provide "pitch" articulation and the second pivot axis $P_2$ could be configured to provide "yaw" articulation.

A plurality of drive cables, shown as drive cables 408a, 408b, 408c, and 408d, extend longitudinally within a lumen 410 defined by the shaft 202 (or a shaft adaptor) and pass through the wrist 206 to be operatively coupled to the end effector 204. The drive cables 408a-d form part of the cable driven motion system briefly described above, and may be referred to and otherwise characterized as cables, bands, lines, cords, wires, woven wires, ropes, strings, twisted strings, elongate members, etc. The drive cables 408a-d can be made from a variety of materials including, but not limited to, metal (e.g., tungsten, stainless steel, etc.) a polymer (e.g., ultra-high molecular weight polyethylene), a synthetic fiber (e.g., KEVLAR®, VECTRAN®, etc.), or any combination thereof. While four drive cables 408a-d are depicted in FIG. 4, more or less than four drive cables 408a-d may be included, without departing from the scope of the disclosure.

The drive cables 408a-d extend proximally from the end effector 204 to the drive housing 208 (FIG. 2) where they are operatively coupled to various actuation mechanisms (e.g., capstans) or devices housed therein to facilitate longitudinal movement (translation) of the drive cables 408a-d within the lumen 410. Selective actuation of the drive cables 408a-d causes corresponding drive cables 408a-d to translate longitudinally within the lumen 410 and thereby cause pivoting movement (articulation) of the end effector 204. Moving a given drive cable 408a-d applies tension (i.e., pull force) to the given drive cable 408a-d in a proximal direction, which causes the given drive cable 408a-d to translate and thereby cause the end effector 204 to move (articulate).

The drive cables 408a-d each extend longitudinally through the first, second, and third linkages 402a-c. In some embodiments, each linkage 402a-c may define four, equidistantly-spaced apertures 412 (only two labeled) configured to guide the drive cables 408a-d through the wrist 206. The apertures 412 of each linkage 402a-c coaxially align when the end effector 204 is in the unarticulated position.

The distal end of each drive cable 408a-d may terminate at the distal linkage 402a, thus operatively coupling each drive cable 408a-d to the end effector 204 and, more particularly, to the lower jaw 212. The distal end of each drive cable 408a-d may be enlarged to facilitate fixed attachment thereof to the end effector 204. In some embodiments, as illustrated, the distal end of each drive cable 408a-d may include a ball crimp 413 (only one shown).

The jaws 210, 212 may be moved between the closed and open positions by pivoting the upper jaw 210 relative to the lower jaw 212. In the illustrated embodiment, the upper jaw 210 may be rotatably coupled (mounted) to the lower jaw 212 at a jaw axle 414. A third pivot axis $P_3$ extends through the jaw axle 414 and is generally perpendicular (orthogonal) to the first pivot axis $P_1$ and parallel to the second pivot axis $P_2$. In this embodiment, the lower jaw 212 remains stationary as the upper jaw 210 pivots about the third pivot axis $P_3$. In other embodiments, the end effector 204 may be designed such that the upper jaw 210 remains stationary as the lower jaw 212 pivots about the third pivot axis $P_3$, without departing from the scope of the disclosure.

A central pulley 416 (partially visible) may be mounted to the jaw axle 414 and receive a jaw cable 418 that may be actuated to selectively open and close the jaws 210, 212. Similar to the drive cables 408a-d, the jaw cable 418 extends longitudinally within the lumen 410 of the shaft 202 and passes through the wrist 206. The jaw cable 418 may form part of the cable driven motion system described herein and, therefore, may extend proximally from the end effector 204 to the drive housing 208 (FIG. 2). The jaw cable 418 may comprise a single line or wire looped around the central pulley 416 and opposing first and second ends 420a and 420b of the jaw cable 418 extend proximally to the drive housing 208. Actuation of corresponding drive inputs will cooperatively cause tension or slack in the jaw cable 418 and thereby cause the upper jaw 210 to rotate about the third pivot axis $P_3$ between the open and closed positions. More specifically, a tensile load assumed on the first end 420a of the jaw cable 418 may operate to close the jaws 210, 212, and a tensile load assumed on the second end 420b of the jaw cable 418 may operate to open the jaws 210, 212. Consequently, the first end 420a of the jaw cable 418 may alternately be referred to as the "closure cable" and the second end 420b of the jaw cable 418 may alternately be referred to as the "open cable."

In some embodiments, an electrical conductor 422 may supply electrical energy to the end effector 204 and, more particularly, to an electrode 424 included in the end effector 204. The electrical conductor 422 extends longitudinally within the lumen 410, through the wrist 206, and terminates at the electrode 424. In some embodiments, the electrical conductor 422 may comprise a wire, but may alternatively comprise a rigid or semi-rigid shaft, rod, or strip (ribbon) made of a conductive material. The electrical conductor 422 may be partially covered with an insulative covering (overmold) made of a non-conductive material. Using the electrical conductor 422 and the electrode 424, the end effector 204 may be configured for monopolar or bipolar operation.

In the illustrated embodiment, the end effector 204 comprises a combination tissue grasper and vessel sealer that includes a cutting element 426 (mostly occluded), alternately referred to as a "knife" or "blade." The cutting element 426 is aligned with and configured to traverse a guide track 428 defined longitudinally in one or both of the upper and lower jaws 210, 212. The cutting element 426 may be operatively coupled to the distal end of a drive rod 430 that extends longitudinally within the lumen 410 and passes through the wrist 206. Longitudinal movement (translation) of the drive rod 430 correspondingly moves the cutting element 426 within the guide track(s) 428. Similar to the drive and jaw cables 408a-d, 418, the drive rod 430 may form part of the cable driven motion system and, therefore, may extend proximally from the cutting element 426 to the drive housing 208 (FIG. 2). Selective actuation of a corresponding drive input will cause the drive rod 430 to move distally or proximally within the lumen 410, and correspondingly move the cutting element 426 in the same direction.

Figure 5:
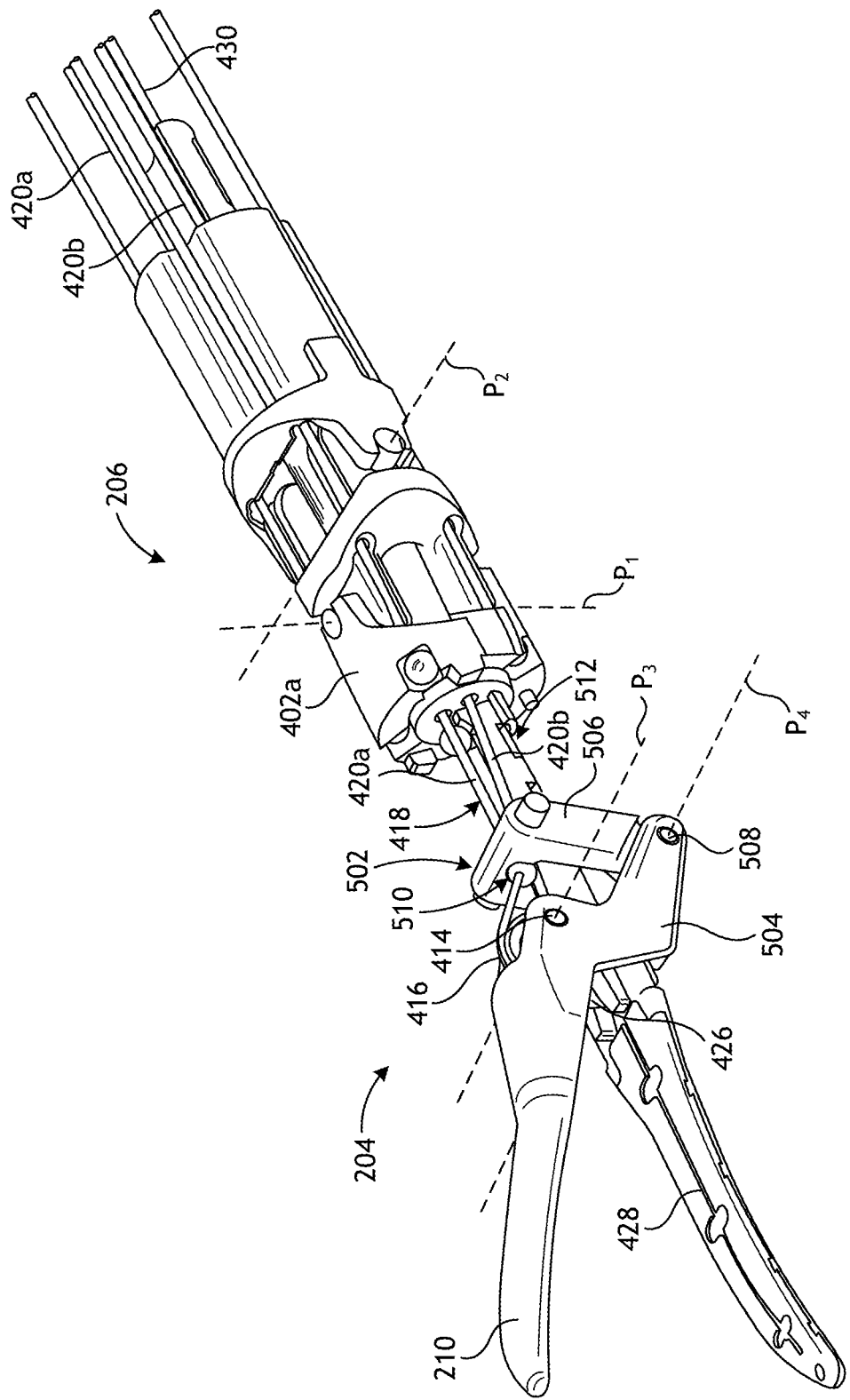
FIG. 5 is an isometric side view of the end effector of FIG. 4 in an open position, according to one or more embodiments.

FIG. 5 is an isometric side view of the end effector 204 in an open position, according to one or more embodiments. More particularly, FIG. 5 depicts the upper jaw 210 pivoted to the open position, and the lower jaw 212 (FIG. 4) is omitted to enable viewing of the internal components of the end effector 204. As illustrated, the end effector 204 includes a pivot link 502 operatively coupled to the upper jaw 210. More specifically, the upper jaw 210 provides or otherwise defines one or more legs 504 (one shown, one occluded) that are pivotably coupled to a corresponding one or more legs 506 (one shown, one occluded) of the pivot link 502 at a pivot axle 508. A fourth pivot axis $P_4$ extends through the pivot axle 508 and may be generally perpendicular (orthogonal) to the first pivot axis $P_1$ and parallel to the second and third pivot axes $P_2$, $P_3$.

The central pulley 416 (mostly occluded) is rotatably supported on the jaw axle 414, and the jaw cable 418 loops around the central pulley 416 and the opposing ends 420a,b of the jaw cable 418 extend proximally through the wrist 206. The jaw cable 418 may be operatively coupled to the pivot link 502 such that movement (i.e., longitudinal translation) of the jaw cable 418 correspondingly moves the pivot link 502. For example, a cable anchor 510 may be secured to or otherwise form part of one proximally extending end 420a,b of the jaw cable 418 and may help operatively couple the jaw cable 418 to the pivot link 502.

To move the jaws 210, 212 to the open position, the jaw cable 418 may be actuated to move the pivot link 502 distally, which may be done, for example, by pulling proximally on the second end 420b of the jaw cable 418 (i.e., the "open cable"). As the pivot link 502 moves distally, the legs 506 of the pivot link 502 act on the legs 504 of the upper jaw 210 at the pivot axle 508 and forces the legs 504 downward in rotation about the fourth pivot axis $P_4$. Downward movement of the legs 504 correspondingly causes the upper jaw 210 to pivot about the third pivot axis $P_3$. As it pivots about the third pivot axis $P_3$, the upper jaw 210 is moved to the open position.

To move the upper jaw 210 back to the closed position, the jaw cable 418 may be actuated to move the pivot link 502 proximally, which may be done by pulling proximally on the first end 420a of the jaw cable 418 (i.e., the "closure cable"). This causes the pivot link 502 to pull upward on the legs 504 of the upper jaw 210 in rotation about the fourth pivot axis $P_4$, and upward movement of the legs 504 correspondingly causes the upper jaw 210 to pivot about the third pivot axis $P_3$ and moves the upper jaw 210 to the closed position.

Figure 6A:
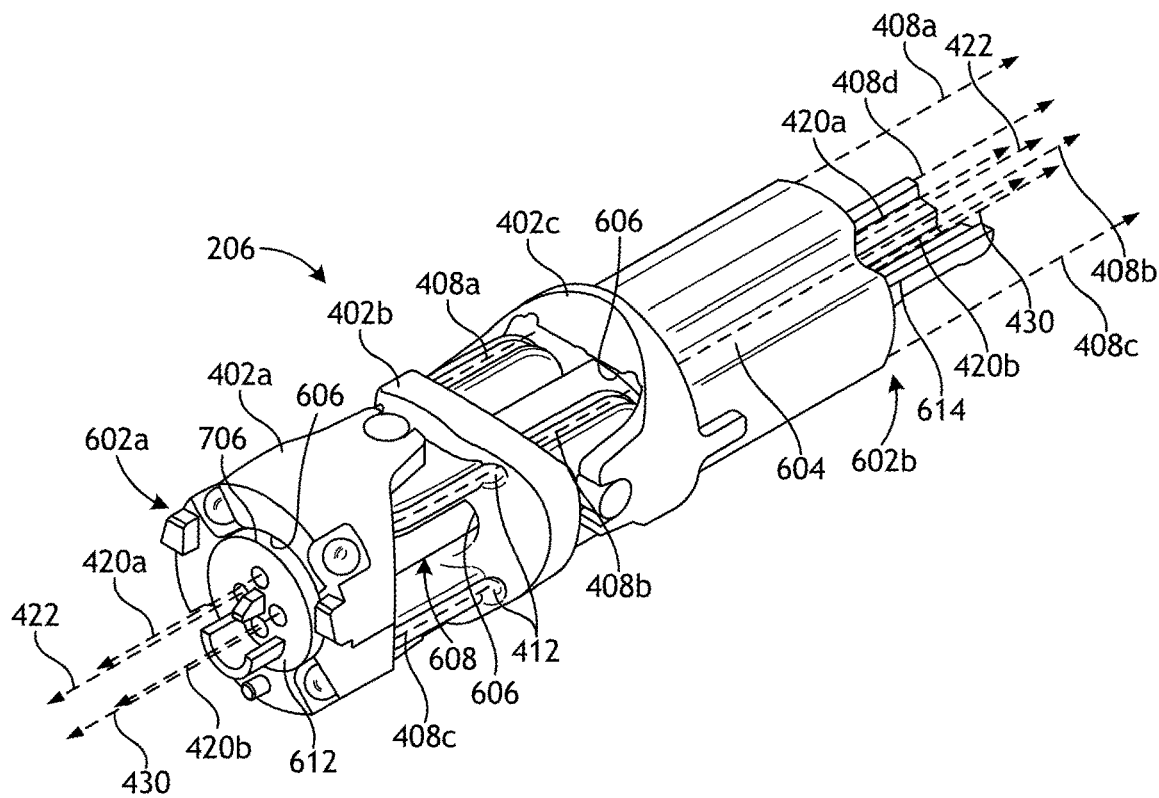
FIGS. 6A and 6B are enlarged isometric front and back views, respectively, of the wrist of FIGS. 4 and 5, according to one or more embodiments.
Figure 6B:
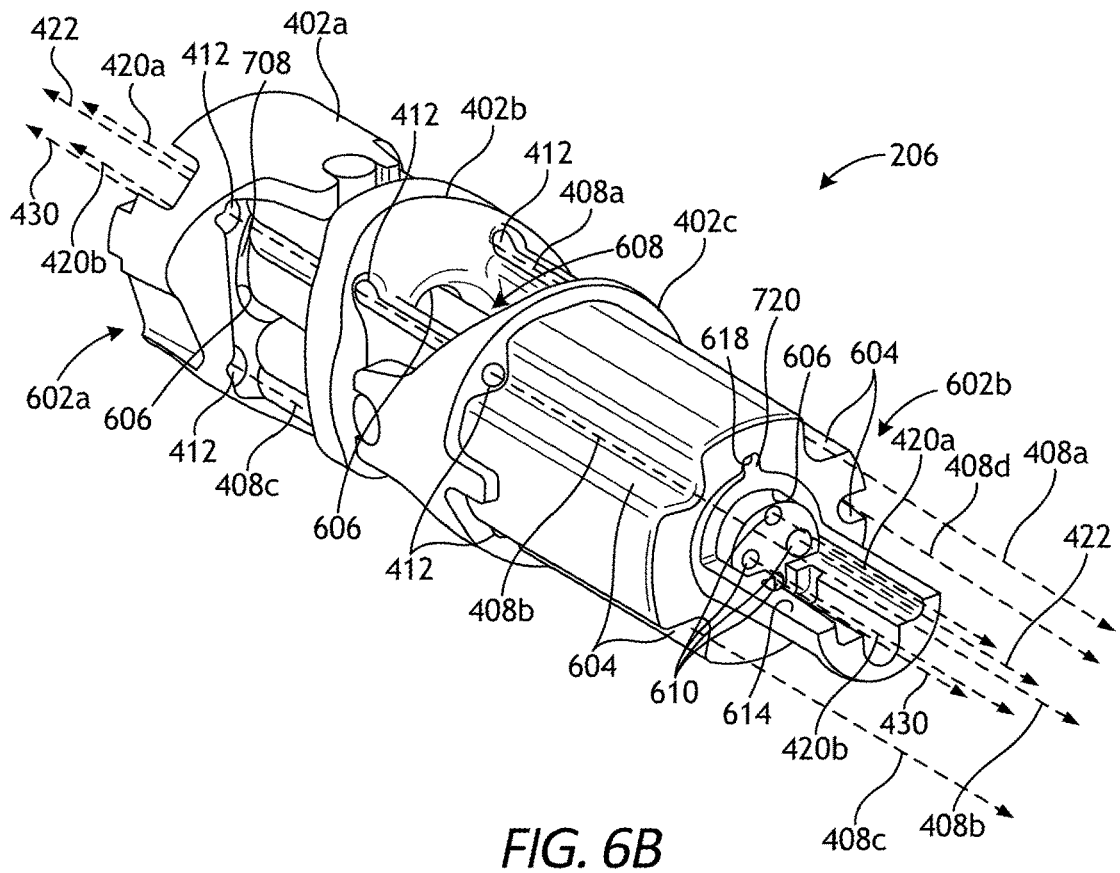

FIGS. 6A and 6B are enlarged isometric front and back views, respectively, of the wrist 206, according to one or more embodiments. The wrist 206 has a first or "distal" end 602a and a second or "proximal" end 602b opposite the distal end 602a. The distal linkage 402a is positioned at the distal end 602a, the proximal linkage 402c is positioned at the proximal end 602b, and the intermediate linkage 402b interposes and operatively couples the distal and proximal linkages 402a,c. However, embodiments are contemplated herein where the intermediate linkage 402b is omitted and the distal and proximal linkages 402a,c are alternatively directly coupled at a common axle.

For simplicity, the drive cables 408a-d, the electrical conductor 422, the first and second ends 420a,b of the jaw cable 418 (FIGS. 4 and 5), and the drive rod 430 are each depicted in FIGS. 6A-6B as dashed lines. The drive cables 408a-d pass through portions (e.g., apertures 412) of the wrist 206 and terminate at the distal linkage 402a. The proximal linkage 402c may provide or otherwise define longitudinal grooves 604 that accommodate each drive cable 408a-d, and each groove 604 may receive a corresponding one of the drive cables 408a-d. The grooves 604 may be aligned with the corresponding apertures 412 defined by the proximal linkage 402c.

The wrist 206 provides or defines a central channel 606 that extends between the distal and proximal ends 602a,b. In embodiments where the wrist 206 includes the distal, intermediate, and proximal linkages 402a-c, corresponding portions of the central channel 606 may be cooperatively and successively defined by each linkage 402a-c. However, in embodiments where the wrist 206 includes only the distal and proximal linkages 402a,c, the central channel 606 may be defined cooperatively and successively by only the distal and proximal linkages 402a,c. The portions of the central channel 606 defined by each linkage 402a-c may coaxially align when the wrist 206 is non-articulated, but move out of axial alignment when the wrist 206 is moved in articulation.

The wrist 206 may further include a flexible member 608 positionable within the central channel 606 and extending at least partially between the first and second ends 602a-b of the wrist 206. As best seen in FIG. 6B, the flexible member 608 may provide or otherwise define one or more conduits 610 (four shown) that extend through the entire length of the flexible member 608. Consequently, the flexible member 608 may be referred to as a "multilumen" or a "multilumen element." The conduits 610 may be configured to receive the electrical conductor 422, the first and second ends 420a,b of the jaw cable 418 (FIGS. 4 and 5), and the drive rod 430, collectively referred to herein as "central actuation members." Accordingly, the central actuation members may penetrate the wrist 206 by extending through the conduits 610 of the flexible member 608.

In some embodiments, as illustrated, the conduits 610 may exhibit a circular cross-sectional shape, but could alternatively exhibit other cross-sectional shapes, such as polygonal, oval, or ovoid, without departing from the scope of the disclosure. Moreover, one or more of the conduits 610 may be lined with a material that helps mitigate abrasion and friction, such as nylon, silicone, nitinol, etc. Furthermore, the size (diameter) of the conduits 610 may vary, depending on the application. Those skilled in the art will readily appreciate that the shape, material, and size of the conduits 610 may be altered or otherwise customized consistent with known industry practices, without departing from the scope of the disclosure.

The flexible member 608 may be operatively coupled to the distal linkage 402a at its distal end, but may be free to move axially relative to the proximal linkage 402c at its proximal end. In some embodiments, for example, the wrist 206 may include a distal adapter 612 (FIG. 6A) and a proximal adapter 614 (FIG. 6B). The distal adapter 612 may operatively couple the flexible member 608 to the distal linkage 402a, and the proximal adapter 612 may be configured to support the flexible member 608 in sliding axial engagement with the proximal linkage 402c. In at least one embodiment, however, the proximal adapter 612 may be omitted and the flexible member 608 may directly contact the proximal linkage 402c in sliding engagement.

Figure 7A:
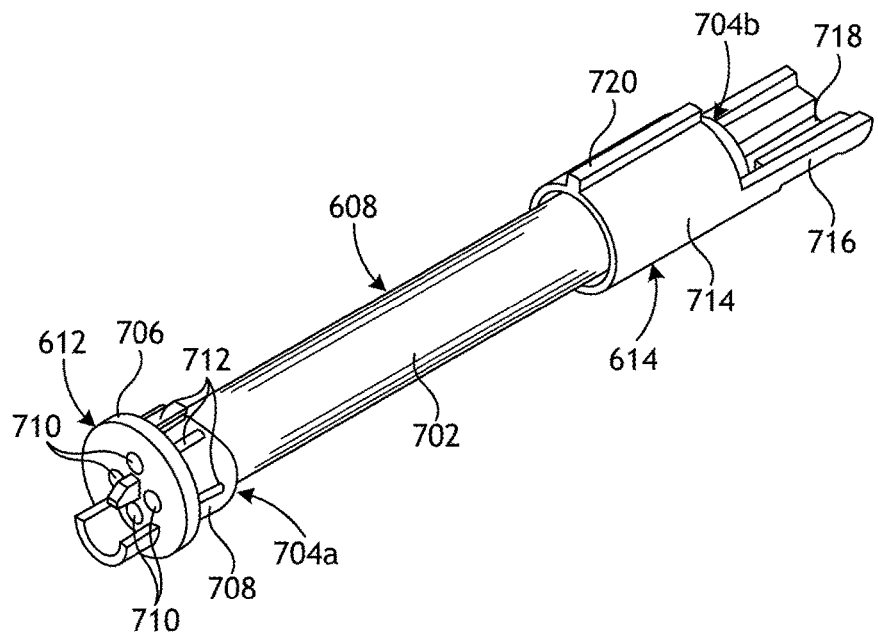
FIGS. 7A and 7B are isometric and exploded views, respectively, of the flexible member and the distal and proximal adapters of FIGS. 6A-6B, according to one or more embodiments.
Figure 7B:
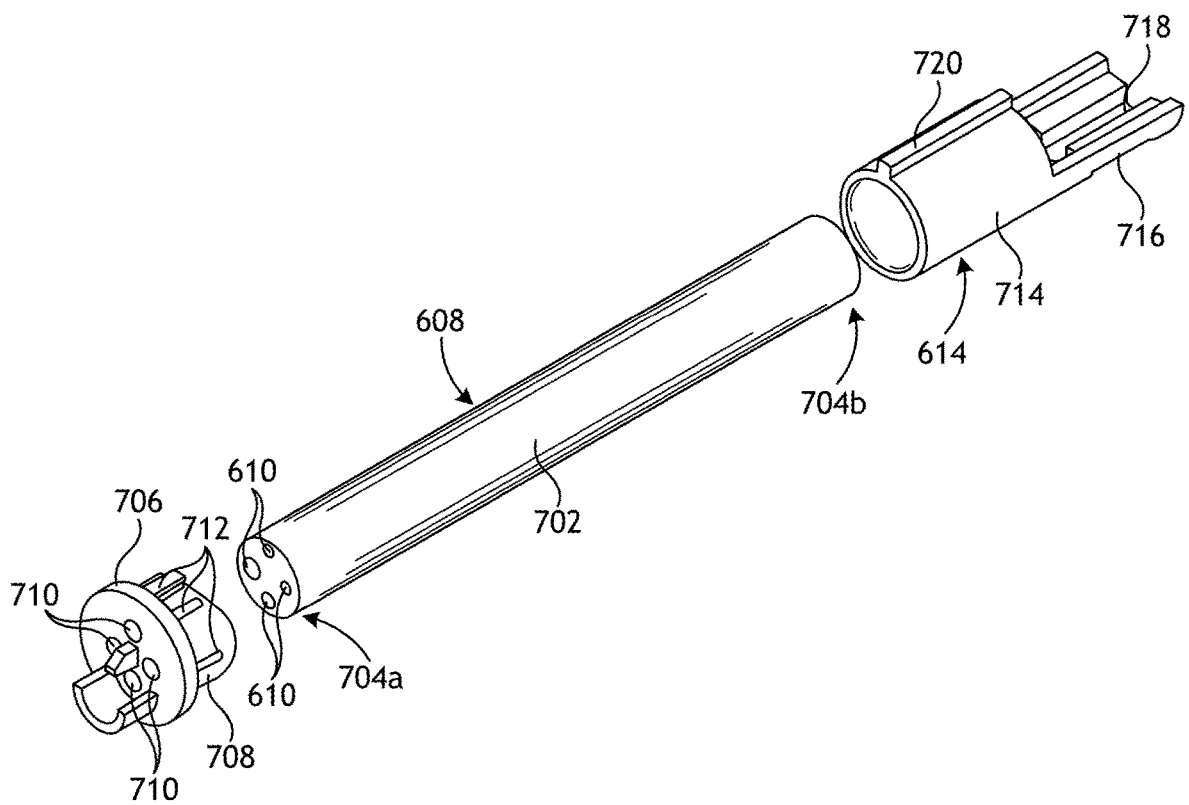

FIGS. 7A and 7B are isometric and exploded views, respectively, of the flexible member 608 and the distal and proximal adapters 612, 614, according to one or more embodiments. As illustrated, the flexible member 608 may comprise a generally cylindrical body 702 having a first or "distal" end 704a and a second or "proximal" end 704b opposite the distal end 704a. In some embodiments, as illustrated, the body 702 may exhibit a substantially circular cross-section, but may alternatively exhibit other cross-sectional shapes, such as polygonal (e.g., triangular, rectangular, etc.), polygonal with rounded corners, oval, ovoid, or any combination thereof, without departing from the scope of the disclosure.

The flexible member 608 may be made of any flexible or semi-flexible material that allows the flexible member 608 to flex or bend when the wrist 206 (FIGS. 6A-6B) articulates. The material for the flexible member 608 may also exhibit low friction characteristics or may otherwise be lubricious, which may prove advantageous in minimizing friction caused by the central actuation members (e.g., the electrical conductor 422, the first and second ends 420a,b of the jaw cable 418, and the drive rod 430 of FIGS. 6A-6B) extending through the conduits 610. Alternatively, the outside diameter of one or more of the central actuation members, such as the first and second ends 420a,b of the jaw cable 418, or the inside diameter of the conduits 610 may be coated with medical grade grease (e.g., KRYTOX™) to reduce contact friction. Furthermore, the material for the flexible member 608 may also exhibit good wear characteristics so the central actuation members do not inadvertently cut through the corresponding conduits 610 following repeated use. The diameter or size of each conduit 610 may be large enough to enable the central actuation members to move therein without substantive obstruction (friction), but small enough to support the central actuation members for longitudinal movement.

Suitable materials for the flexible member 608 include, but are not limited to, polytetrafluoroethylene (PTFE or TEFLON®), silicone, nylon, a thermoplastic polyurethane (TPU, e.g., CARBOTHANE™, PELLETHANE®, TECOBAX™), a thermoplastic elastomer (TPE, e.g., PEBAX®), or any combination thereof. In at least one embodiment, the flexible member 608 may comprise an extrusion or may otherwise be manufactured through an extrusion process. In other embodiments, the flexible member 608 may be printed through an additive manufacturing process (e.g., 3D printing). In some embodiments, the flexible member 608 can be manufactured from a plastic resin blended with a lubricant, such as PTFE solid particles blended with PROPEL® as a liquid lubricating additive.

The distal adapter 612 may be made of a rigid or semi-rigid material including, but not limited to, a plastic, a metal, a composite material, and any combination thereof. Example materials for the distal adapter 612 include, but are not limited to, polyetherimide, polycarbonate, polystyrene, and nylon. In some embodiments, as illustrated, the distal adapter 612 may provide or otherwise define a radial shoulder 706 and a flange 708 that extends from the radial shoulder 706. The flange 708 may be sized to receive the distal end 704a of the flexible member 608. In other embodiments, however, the flange 708 may be omitted and the distal adapter 612 may nonetheless be coupled to the flexible member 608.

The distal adapter 612 may be coupled (fixed) to the distal end 704a of the flexible member 608 via a variety of attachment means. Suitable attachment means include, but are not limited to, bonding (e.g., an adhesive), welding (e.g., sonic or ultrasonic welding), overmolding the distal adapter 612 onto the distal end 704a, an interference or shrink fit, or any combination thereof.

The distal adapter 612 may define one or more or apertures 710 (four shown) configured to co-axially align with the conduits 610 of the flexible member 608. Accordingly, the central actuation members extending through the flexible member 608 (e.g., the electrical conductor 422, the first and second ends 420a,b of the jaw cable 418, and the drive rod 430 of FIGS. 6A-6B) may each exit the flexible member 608 and extend through the distal adapter 612 at the apertures 710.

In some embodiments, the distal adapter 612 may provide one or more features 712 configured to mate with one or more corresponding features of the distal linkage 402a (FIGS. 6A-6B). In the illustrated embodiment, the features 712 are defined on the flange 708, but could alternatively be defined on any other portion of the distal adapter 612, without departing from the scope of the disclosure. Mating the features 712 of the distal adapter 612 with the corresponding features of the distal linkage 402a may help rotationally fix the distal end 704a of the flexible member 608 at the distal end 602a (FIGS. 6A-6B) of the wrist 206 (FIGS. 6A-6B).

The proximal adapter 614 may be made of a rigid or semi-rigid material including, but not limited to, a plastic, a metal, a composite material, or any combination thereof. Example materials for the proximal adapter 614 include, but are not limited to, polyetherimide, polycarbonate, polystyrene, and nylon. The proximal adapter 614 may provide a generally annular body 714 sized to receive the proximal end 704b of the flexible member 608. In some embodiments, the proximal end 704b may extend entirely through the annular body 714, but may alternatively extend only partially therethrough.

The proximal adapter 614 may be coupled (fixed) to the proximal end 704b of the flexible member 608 via a variety of attachment means. Suitable attachment means include, but are not limited to, bonding (e.g., an adhesive), welding (e.g., sonic or ultrasonic welding), overmolding the proximal adapter 614 onto the proximal end 704b, an interference or shrink fit, or any combination thereof.

In some embodiments, a flange 716 may extend proximally from the body 714 of the proximal adapter 614 and may provide or define a groove 718 co-axially alignable with one of the conduits 610. The groove 718 may be sized to receive one of the central actuation members, such as the drive rod 430 (FIGS. 5 and 6A-6B), which may prove advantageous in helping to prevent buckling of the drive rod 430 during operation.

The proximal adapter 614 may provide one or more features 720 matable with one or more corresponding features provided by the proximal linkage 402c (FIGS. 6A-6B). As discussed in more detail below, the feature 720 may comprise a longitudinal rib that may be configured to mate with a longitudinal channel of the proximal linkage 402c.

Referring again to FIGS. 6A-6B, in some embodiments, the distal adapter 612 may be partially received within the central channel 606 defined in the distal linkage 402a. More specifically, the flange 708 (see FIG. 6B) of the distal adapter 612 may extend into the central channel 606 until the radial shoulder 706 (see FIG. 6A) of the distal adapter 612 engages the distal end 602a of the wrist 206 and, more particularly, the distal linkage 402a. In some embodiments, one or more features (not shown) may be defined on the inner radial surface of the central channel 606 at the distal linkage 402a and configured to mate with the features 712 (FIGS. 7A-7B) of the distal adapter 612. Mating these features may help rotationally fix the distal adapter 612 relative to the distal end 602a (FIGS. 6A-6B) of the wrist 206 (FIGS. 6A-61B).

The distal adapter 612 may be arranged to interpose the lower jaw 212 (FIG. 4) and the distal linkage 402a within the assembly of the end effector 204 (FIGS. 4-5), thus restraining (trapping) the distal adapter 612 between the lower jaw 212 and the distal linkage 402a. Since the distal adapter 612 may be fixed to the distal end 704a (FIGS. 7A-7B) of the flexible member 608, restraining (trapping) the distal adapter 612 between the lower jaw 212 and the distal linkage 402a may correspondingly fix the flexible member 608 in place at the distal end 602a of the wrist 206.

Referring specifically to FIG. 6B, the proximal linkage 402c may provide or define a feature 618 sized and otherwise configured to receive (mate with) the feature 720 provided by the proximal adapter 614. In the illustrated embodiment, the feature 618 comprises a longitudinal channel, and the feature 720 comprises a longitudinal rib matable with the longitudinal channel. Mating the features 618, 720 may help rotationally fix the flexible member 608 to the proximal linkage 402c, but also allows the flexible member 608 to move longitudinally relative to the proximal linkage 402c. For example, as the wrist 206 articulates, the feature 720 of the proximal adapter 614 may slide relative to the feature 618 of the proximal linkage 402c. In some embodiments, however, the proximal adapter 614 may be omitted and the feature 720 may alternatively be provided by the flexible member 608, without departing from the scope of the disclosure. In other embodiments, the flexible member 608 may be molded or otherwise formed in a shape that lends itself to be rotationally fixed to the proximal linkage 402c, such as a square or "D" shape.

In example operation of the wrist 206, the drive cables 408a-d are selectively actuated to articulate the wrist 206. As the wrist 206 articulates, the flexible member 608 correspondingly bends or flexes, and the central actuation members (e.g., the electrical conductor 422, the first and second ends 420a,b of the jaw cable 418, and the drive rod 430) will correspondingly move in the direction of articulation and thereby lengthen or shorten, depending on the bend direction. Extending the central actuation members through the conduits 610 of the flexible member 608 creates a defined and predictable pathway for each central actuation member.

Undesirable movement at the tip of the end effector 204 (FIG. 2) can occur when a high closure force is applied to the closure cable (e.g., the first end 420a of the jaw cable 418) to clamp the jaws 210, 212 onto tissue. This jaw tip motion is generated by slight off-center positional offsets of the closure cable at one or both of the articulation joints (i.e., the first and second pivot axes $P_1$, $P_2$ of FIGS. 4-5) during movement. This creates an unbalancing moment that can cause the jaws 210, 212 to move abruptly or "dive" in the direction of the imbalance. This "tip dive" is unexpected and undesirable when clamping critical structures.

According to embodiments of the present disclosure, one or more sub-articulation pivot guides may be included (installed) in the wrist 206 at the articulation joints to help contain and support the outer diameter of the flexible member 608 and thereby limit its ability to flex beyond the pivot axes $P_1$, $P_2$. As a result, the closure cable (or any of the central actuation members) will also be prevented from deviating below the pivot axes $P_1$, $P_2$ during actuation and tip dive will be mitigated. Similarly, the open cable may extend through a conduit 610 angularly offset 90° from the closure cable. The open cable interfaces with the sub-articulation pivot guide at the second articulation joint (i.e., the yaw axis) in the same manner as the closure cable. As the jaws 210, 212 are opened against resisting tissue, the tension in the open cable increases, and the potential for tip dive in the yaw axis increases. The sub-articulation pivot guide arranged at the second articulation joint will resist the offset moment and any resulting motion of the flexible member 608 in this direction.

Figure 8A:
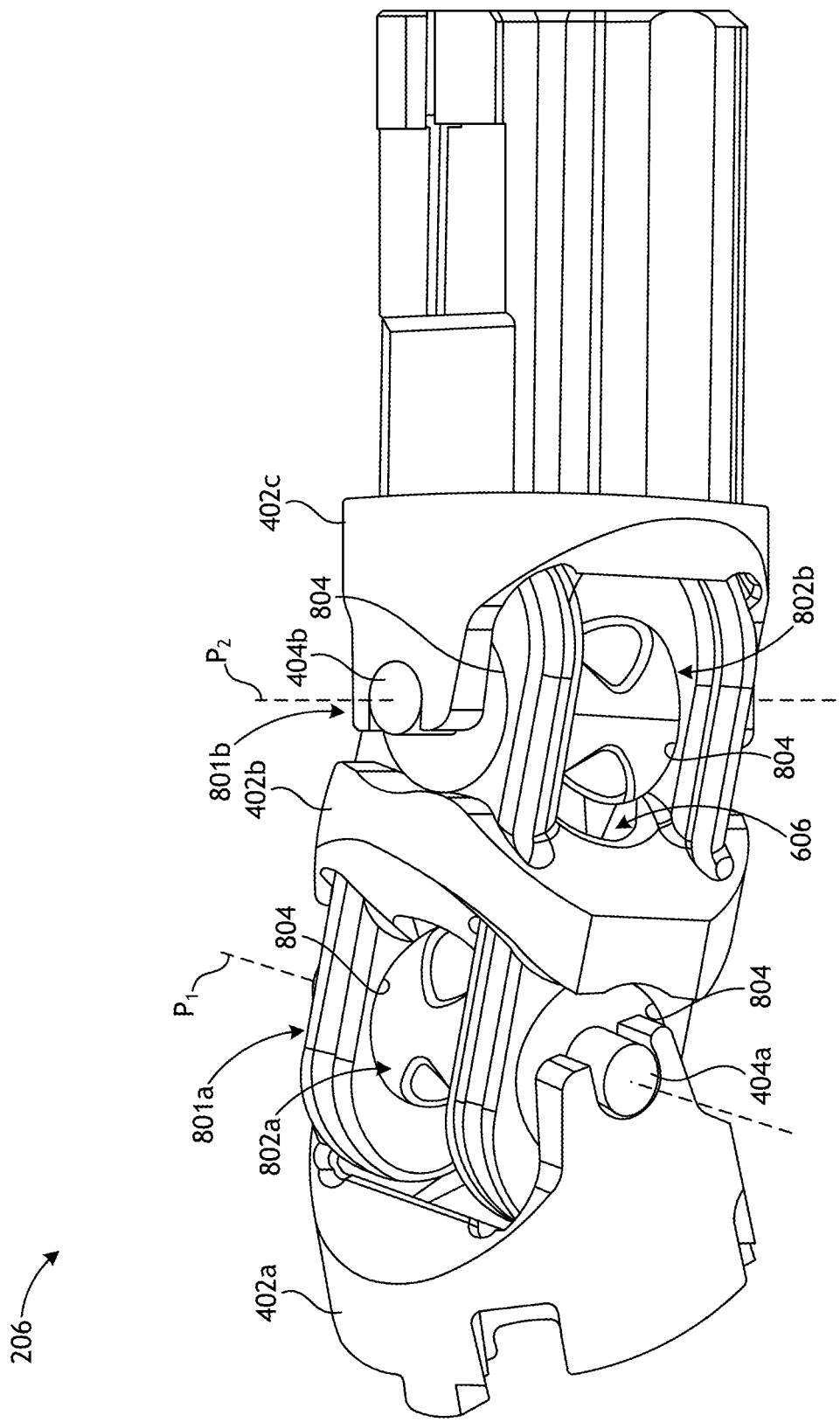
FIG. 8A is a side view of an example embodiment of the wrist of FIGS. 4, 5, and 6A-6B that may incorporate one or more principles of the present disclosure.

FIG. 8A is a side view of an example embodiment of the wrist 206 that may incorporate one or more principles of the present disclosure. For simplicity, the drive cables 408a-d (FIGS. 4-5), the electrical conductor 422 (FIGS. 4-5), the first and second ends 420a,b of the jaw cable 418 (FIGS. 4-5), and the drive rod 430 (FIGS. 4-5) are each omitted in FIG. 8A. Also omitted is the flexible member 608 (FIGS. 6A-6B and 7A-7B) that would otherwise extend through the central channel 606 of the wrist 206 and accommodate the central actuation members (e.g., the electrical conductor 422, the first and second ends 420a,b of the jaw cable 418, and the drive rod 430).

As illustrated, the wrist 206 includes the distal linkage 402a, rotatably coupled to the intermediate linkage 402b at a first articulation joint 801a, and the proximal linkage 402c rotatably coupled to the intermediate linkage 402b at a second articulation joint 801b. The first pivot axis $P_1$ extends through the first articulation joint 801a and facilitates "yaw" movement (articulation) of the end effector 204 (FIG. 2), and the second pivot axis $P_2$ extends through the second articulation joint 801b and facilitates "pitch" movement (articulation) of the end effector 204. In some embodiments, the wrist 206 may alternatively include only the intermediate linkage and one of the distal or proximal linkages 402a,c. In such embodiments, the wrist 206 would only have one articulation joint capable of facilitating either "yaw" or "pitch" movement, depending on the orientation of the associated pivot axis.

The wrist 206 also includes a first pivot guide 802a arranged at the first articulation joint 801a, and a second pivot guide 802b arranged at the second articulation joint 801b. While the present embodiment includes pivot guides 802a,b at each articulation joint 801a,b, it is contemplated herein to employ only one of the pivot guides 802a,b at a corresponding one of the articulation joints 801a,b.

In the illustrated embodiment, each pivot guide 802a,b is rotatably mounted to the intermediate linkage 402b by extending at least partially through opposing apertures 804 defined near each end of the intermediate linkage 402b. Moreover, the pivot guides 802a,b are rotatable about the first and second pivot axes $P_1$, $P_2$, respectively, and, in the illustrated embodiment, the pivot guides 802a,b provide or otherwise define the first and second axles 404a,b, respectively. Accordingly, the distal linkage 402a may be rotatably coupled to the intermediate linkage 402b via the first axle 404a provided by the first pivot guide 802a, and the proximal linkage 402c may be rotatably coupled to the intermediate linkage 402b via the second axle 404b provided by the second pivot guide 802b.

In some embodiments, one or both of the pivot guides 802a,b may be made of an electrically-conductive material to help act as a ground to the conductor 422 (FIGS. 4-5), which may be grounded to the distal linkage 402a (FIG. 8A). In other embodiments, one or both of the pivot guides 802a,b may be made of any rigid or semi-rigid material including, but not limited to, a plastic (polymer), a metal, a composite material, an elastomer, or any combination thereof. Example non-metal materials include, but are not limited to, polyetherimide (e.g., ULTEM®), polycarbonate, polystyrene, poly ether ether ketone (PEEK), carbon filled polyphalamide (PPA), and nylon. In at least one embodiment, one or both of the pivot guides 802a,b may be made of two or more materials, such as an overmold.

Figure 8B:
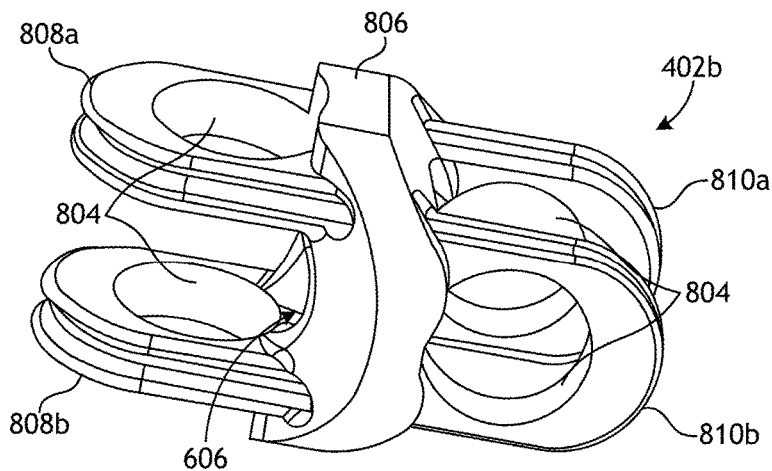
FIG. 8B is an enlarged isometric view of an embodiment of the intermediate linkage of FIG. 8A.

FIG. 8B is an enlarged isometric view of one embodiment of the intermediate linkage 402b. In the illustrated embodiment, the intermediate linkage 402b includes a main body 806 that defines a portion of the central channel 606 and configured to accommodate the flexible member 608 (FIGS. 6A-6B and 7A-7B). A pair of distally extending lobes 808a and 808b extend distally from the body 806 and are laterally offset from each other, and a pair of proximally extending lobes 810a and 810b extend proximally from the body 806 and are laterally offset from each other. The proximally extending lobes 810a,b are angularly offset from the distally extending lobes 808a,b by 90°, which allows the intermediate linkage 402b to facilitate both "yaw" and "pitch" articulation of the end effector 204 (FIG. 2). Each lobe 808a,b and 810a,b defines an aperture 804 sized to rotatably receive a portion of the corresponding pivot guide 802a,b, as mentioned above.

Figure 8C:
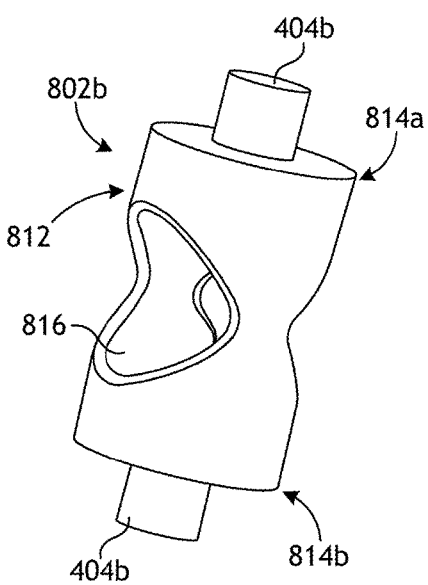
FIG. 8C is enlarged isometric view of the second pivot guide of FIG. 8A.

FIG. 8C is an enlarged isometric view of the second pivot guide 802b. Since the first and second pivot guides 802a,b are substantially similar in structure and operation, discussion of the second pivot guide 802b will equally apply to the first pivot guide 802a. As illustrated, the second pivot guide 802b includes a generally cylindrical body 812 having a first end 814a and a second end 814b opposite the first end 814a. The first and second ends 814a,b may be rotatably received into the apertures 804 defined on the proximally extending lobes 810a,b (FIG. 8B) of the intermediate linkage 402b (FIG. 8B), as mentioned above. Moreover, protrusions extending outward from each end 814a,b of the body 812 help form or otherwise provide the second axle 404b for the wrist 206 (FIG. 8A). Furthermore, the cylindrical body 812 may define a central aperture 816 alignable with the central channel 606 (FIGS. 8A-8B) of the wrist 206 and sized or otherwise configured to accommodate the flexible member 608 (FIGS. 6A-6B and 7A-7B) therethrough.

Figure 8D:
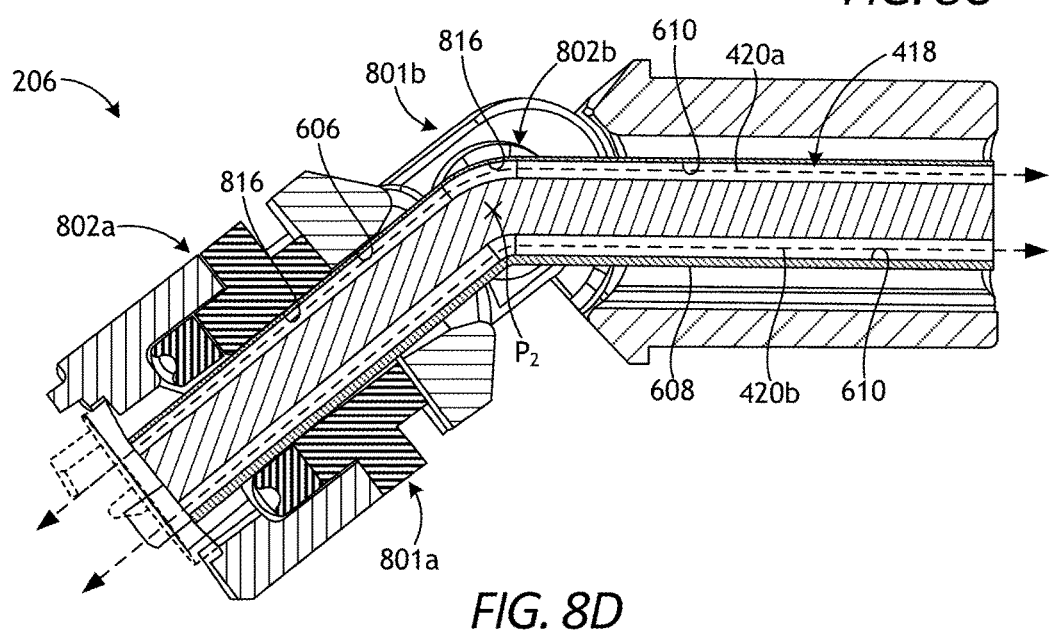
FIG. 8D is a cross-sectional view of the wrist of FIG. 8A in example operation, according to one or more embodiments.

FIG. 8D is a cross-sectional side view of the wrist 206 of FIG. 8A demonstrating example operation, according to one or more embodiments. As illustrated, the flexible member 608 is extended through the central channel 606 of the wrist 206 and also through the central aperture 816 of each pivot guide 802a,b. The first and second ends 420a,b of the jaw cable 418 are shown as dashed lines extending through corresponding conduits 610 defined through the flexible member 608.

As depicted, the wrist 206 is being articulated in pitch motion at the second articulation joint 801b and otherwise moved about the second pivot axis $P_2$. Moving the second articulation joint 801b correspondingly causes the second pivot guide 802b to rotate about the pivot axis $P_2$ to accommodate bending (flexure) of the flexible member 608 as it flexes from a straight position. As the angle at the second articulation joint 801b deviates from straight, the flexible member 608 will be urged to dip above or below the second pivot axis $P_2$ (depending on the articulation direction). Moreover, as the closure cable (i.e., the first end 420a of the jaw cable 418) tightens with clamp load, it will tend to find the shortest path through the second articulation joint 801b, which may further urge the flexible member 608 to dip below the second pivot axis $P_2$.

The second pivot guide 802b, however, helps to contain and support the outer diameter of the flexible member 608 at the second articulation joint 801b and thereby prevents the flexible member 608 from flexing beyond the second pivot axis $P_2$. Consequently, the centerline of the closure cable (i.e., the first end 420a of the jaw cable 418) will also not be able to deviate below the second pivot axis $P_2$ during clamping, which will mitigate tip dive at the end effector 204 (FIG. 2).

While the foregoing description is focused on operation of the second pivot guide 802b during articulation at the second articulation joint 801b, the first pivot guide 802a may operate similarly during articulation at the first articulation joint 801a in yaw movement. Moreover, it is contemplated herein that material properties (e.g., hardness, lubricity, etc.) of the pivot guides 802a,b (and any of the other pivot guides described herein) may be optimized to improve wear against the flexible member 608 extending through the central apertures 816 of each pivot guide 802a,b. Internal surfaces of the central aperture 816, for example, may be smoothed, curved, and/or include a lubricant, which may help improve articulation joint friction and reduce galling in the surgical tool 200 (FIG. 2), thus increasing device mission life.

Figure 9A:
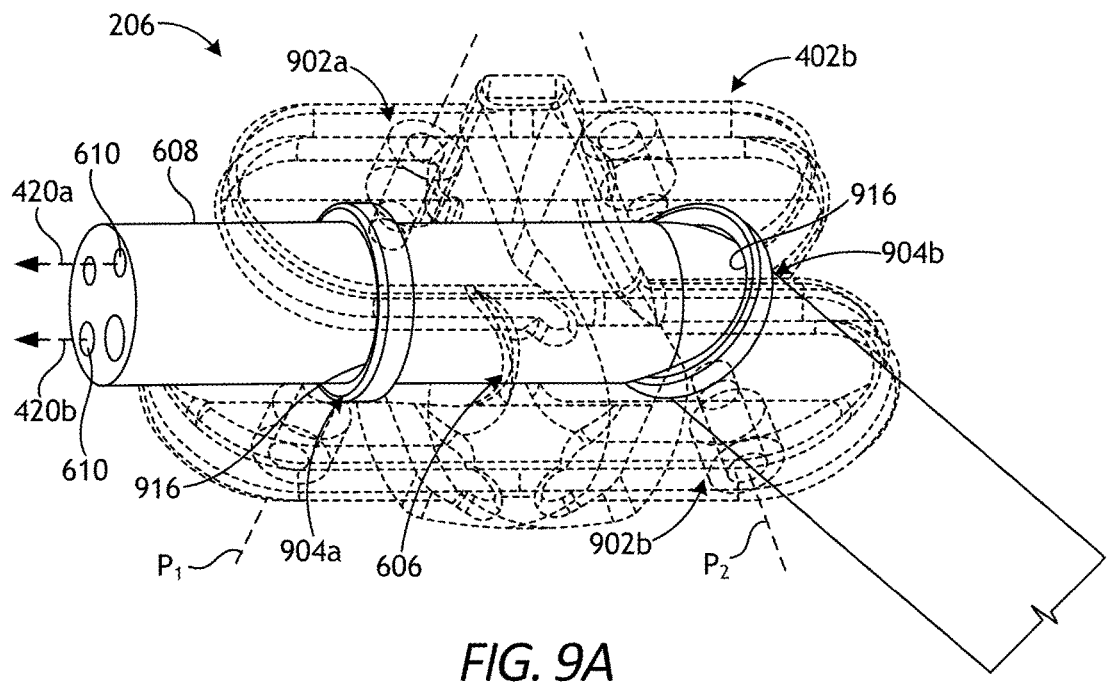
FIG. 9A is an isometric side view of another example embodiment of the wrist of FIGS. 4, 5, and 6A-6B that may incorporate one or more principles of the present disclosure.

FIG. 9A is an isometric side view of another example embodiment of a portion of the wrist 206 that may incorporate one or more principles of the present disclosure. In the illustrated view, the intermediate linkage 402b is shown in phantom to enable viewing of the inner component parts of the wrist 206. The distal and proximal linkages 402a,c (FIGS. 4-5), the drive cables 408a-d (FIGS. 4-5), the electrical conductor 422 (FIGS. 4-5), the first and second ends 420a,b of the jaw cable 418 (FIGS. 4-5), and the drive rod 430 (FIGS. 4-5) are each omitted for simplicity, but would otherwise be included in a full assembly of the wrist 206.

As illustrated, the flexible member 608 extends through the central channel 606 partially defined by intermediate linkage 402b. The first pivot axis $P_1$ extends through a first articulation joint 902a and facilitates "yaw" movement (articulation) of the end effector 204 (FIG. 2), and the second pivot axis $P_2$ extends through a second articulation joint 902b and facilitates "pitch" movement (articulation) of the end effector 204.

The wrist 206 further includes a first pivot guide 904a arranged at the first articulation joint 902a and a second pivot guide 904b arranged at the second articulation joint 902b. Each pivot guide 904a,b is rotatably mounted to the intermediate linkage 402b at the corresponding articulation joints 902a,b and is rotatable about the first and second pivot axes $P_1$, $P_2$, respectively. The pivot guides 904a,b may be made of any semi-rigid or flexible material including, but not limited to, a plastic, a metal, a composite material, an elastomer, or any combination thereof. Example non-metal materials include, but are not limited to, polyetherimide, polycarbonate, polystyrene, carbon filled polyphalamide (PPA), and nylon.

Figure 9B:
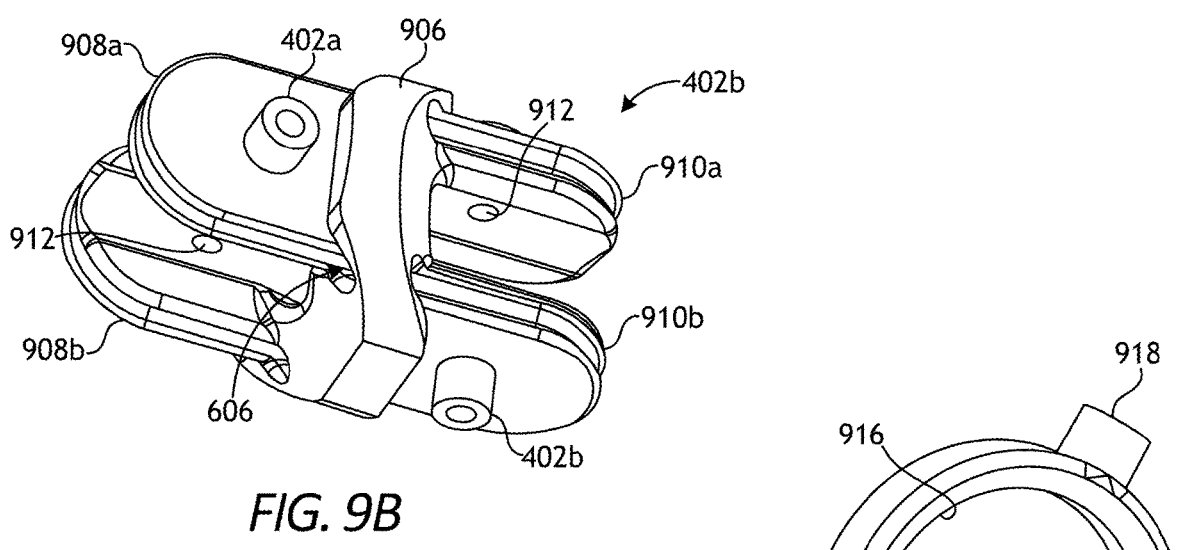
FIG. 9B is an enlarged isometric view of an embodiment of the intermediate linkage of FIG. 9A.

FIG. 9B is an enlarged isometric view of another embodiment of the intermediate linkage 402b. In the illustrated embodiment, the intermediate linkage 402b includes a main body 906 that defines a portion of the central channel 606 configured to accommodate the flexible member 608 (FIG. 9A). A pair of distally extending lobes 908a and 908b extend distally from the body 906 and are laterally offset from each other, and a pair of proximally extending lobes 910a and 910b extend proximally from the body 906 and are laterally offset from each other. The proximally extending lobes 910a,b are angularly offset from the distally extending lobes 908a,b by 90°, which allows the intermediate linkage 402b to facilitate both "yaw" and "pitch" articulation of the end effector 204 (FIG. 2). Each lobe 908a,b and 910a,b defines an aperture 912 sized to rotatably receive a portion of the corresponding pivot guide 904a,b. Moreover, the lobes 908a,b and 910a,b provide portions of the first and second axles 404a,b, respectively, to enable rotatable coupling to the distal and proximal linkages 402a,c (FIGS. 4-5).

Figure 9C:
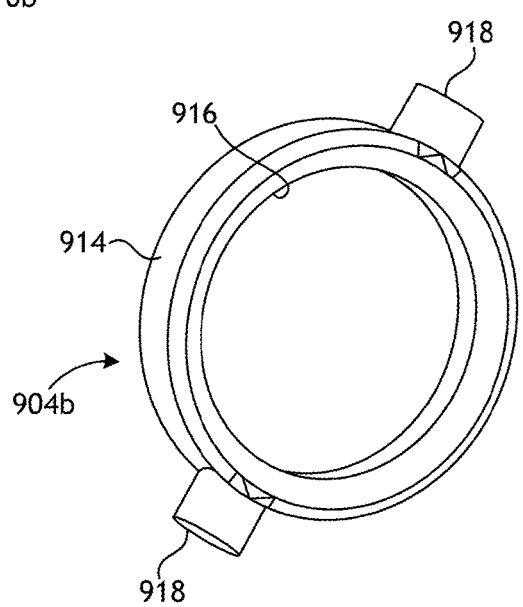
FIG. 9C is enlarged isometric view of the second pivot guide of FIG. 9A.

FIG. 9C is an enlarged isometric view of the second pivot guide 904b. Since the first and second pivot guides 904a,b are substantially similar in structure and operation, discussion of the second pivot guide 904b will equally apply to the first pivot guide 904a. As illustrated, the second pivot guide 904b includes a generally annular body 914 that defines a central aperture 916 alignable with the central channel 606 (FIGS. 9A-9B) of the wrist 206 (FIG. 9A) and sized or otherwise configured to accommodate the flexible member 608 (FIG. 9A) therethrough. Opposing pins 918 may extend radially outward from the annular body 914 at angularly opposite sides of the body 914. To secure the second pivot guide 904b to the intermediate linkage 402b, the pins 918 may be rotatably received into the apertures 912 defined on the proximally extending lobes 910a,b (FIG. 9B) of the intermediate linkage 402b (FIG. 9B).

Referring again to FIG. 9A, example operation of the wrist 206 will now be provided, according to one or more embodiments. As illustrated, the flexible member 608 is extended through the central channel 606 of the wrist 206 and also through the central aperture 916 of each pivot guide 904a,b. The first and second ends 420a,b of the jaw cable 418 are shown as dashed lines extending through corresponding conduits 610 defined through the flexible member 608. As depicted, the wrist 206 is being articulated in pitch motion at the second articulation joint 902b and otherwise moved about the second pivot axis $P_2$. Moving the second articulation joint 902b correspondingly causes the second pivot guide 904b to rotate about the second pivot axis $P_2$ to accommodate bending of the flexible member 608 from a straight position. As the angle at the second articulation joint 902b deviates from straight, the flexible member 608 and the closure cable (i.e., the first end 420a of the jaw cable 418) will tend to find the shortest path through the second articulation joint 902b, which can urge the flexible member 608 and the closure cable to dip below the second pivot axis $P_2$, which can cause tip dive if the closure cable is actuated.

The second pivot guide 904b, however, helps to contain and support the outer diameter of the flexible member 608 at the second articulation joint 902b and thereby prevents the flexible member 608 from flexing beyond the second pivot axis $P_2$. Consequently, the centerline of the closure cable (i.e., the first end 420a of the jaw cable 418) will also not be able to deviate below the second pivot axis $P_2$ during clamping, which will mitigate tip dive at the end effector 204 (FIG. 2).

While the foregoing description is focused on operation of the second pivot guide 904b during articulation at the second articulation joint 902b, the first pivot guide 904a may operate similarly during articulation at the first articulation joint 902a in yaw movement.

Figure 10A:
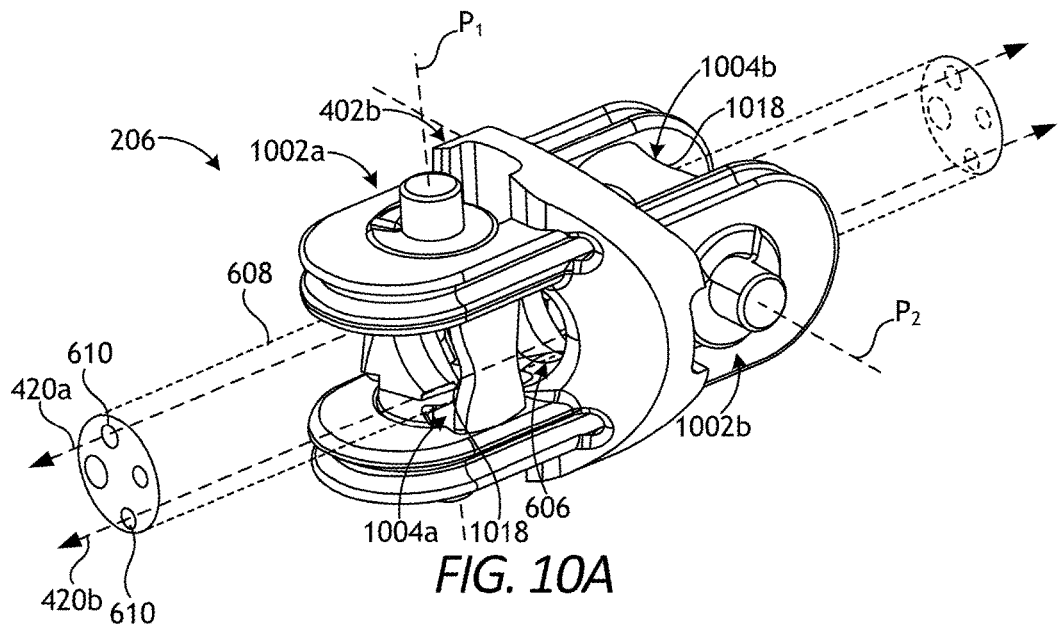
FIG. 10A is an isometric side view of another example embodiment of a portion of the wrist of FIGS. 4, 5, and 6A-6B that may incorporate one or more principles of the present disclosure.

FIG. 10A is an isometric side view of another example embodiment of a portion of the wrist 206 that may incorporate one or more principles of the present disclosure. In the illustrated view, the distal and proximal linkages 402a,c (FIGS. 4-5) are omitted and the flexible member 608 is depicted in phantom and extending through the central channel 606 partially defined by the intermediate linkage 402b. The first pivot axis $P_1$ extends through a first articulation joint 1002a and facilitates "yaw" movement (articulation) of the end effector 204 (FIG. 2), and the second pivot axis $P_2$ extends through a second articulation joint 1002b and facilitates "pitch" movement (articulation) of the end effector 204.

The wrist 206 further includes a first pivot guide 1004a arranged at the first articulation joint 1002a and a second pivot guide 1004b arranged at the second articulation joint 1002b. Each pivot guide 1004a,b is rotatably mounted to the intermediate linkage 402b at the corresponding articulation joints 902a,b and is rotatable about the first and second pivot axes $P_1$, $P_2$, respectively. The pivot guides 1004a,b may be made of any of the materials mentioned herein for any of the pivot guides described herein.

Figure 10B:
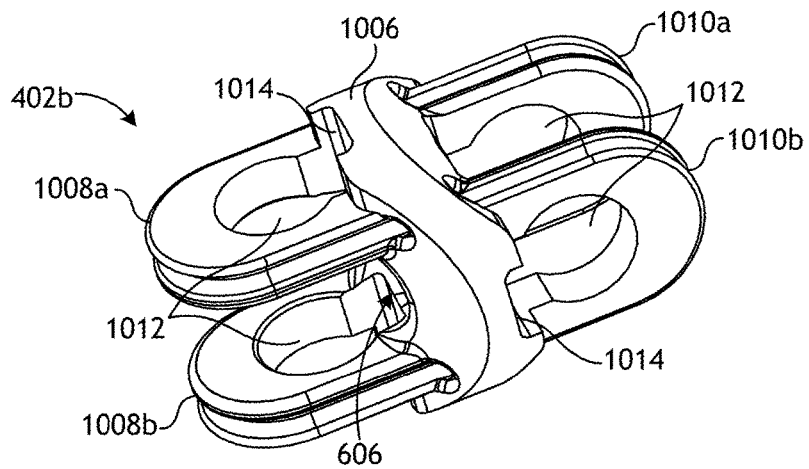
FIG. 10B is an enlarged isometric view of another embodiment of the intermediate linkage of FIG. 10A.

FIG. 10B is an enlarged isometric view of another embodiment of the intermediate linkage 402b. In the illustrated embodiment, the intermediate linkage 402b includes a main body 1006 that defines a portion of the central channel 606 configured to accommodate the flexible member 608 (FIG. 10A). A pair of distally extending lobes 1008a and 1008b extend distally from the body 1006 and are laterally offset from each other, and a pair of proximally extending lobes 1010a and 1010b extend proximally from the body 1006 and are laterally offset from each other. The proximally extending lobes 1010a,b are angularly offset from the distally extending lobes 1008a,b by 90°, which allows the intermediate linkage 402b to facilitate both "yaw" and "pitch" articulation of the end effector 204 (FIG. 2). Each lobe 1008a,b and 1010a,b defines an aperture 1012 sized to rotatably receive a portion of the corresponding pivot guide 1004a,b.

Cutouts 1014 may be defined on opposing sides of the main body 1006. As illustrated, the cutouts 1014 extend orthogonal to each other and are contiguous with the apertures 1012 defined in the corresponding lobes 1008a,b and 1010a,b. As described below, the cutouts 1014 may be used to rotatably mount the pivot guides 1004a,b (FIG. 10A) to the corresponding lobes 1008a,b and 1010a,b.

Figure 10C:
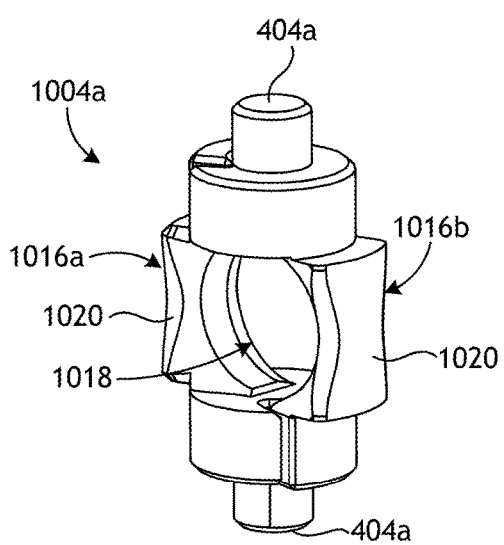
FIGS. 10C and 10D are enlarged isometric and exploded views, respectively, of the first pivot guide of FIG. 10A.
Figure 10D:
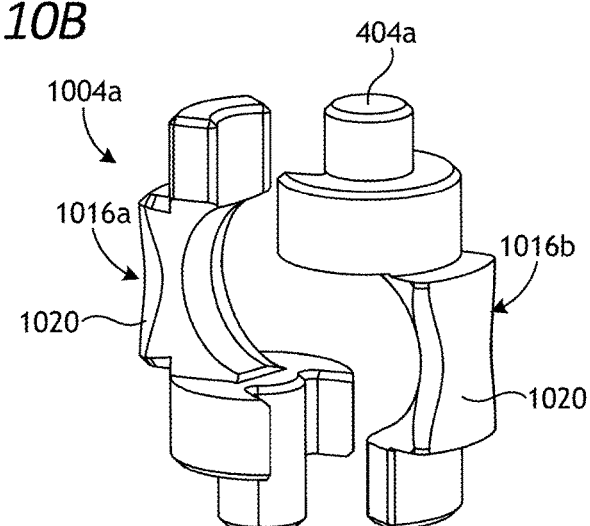

FIGS. 10C and 10D are enlarged assembled and exploded views, respectively, of the first pivot guide 1004a. Since the first and second pivot guides 1004a,b are substantially similar in structure and operation, discussion of the first pivot guide 1004a will equally apply to the second pivot guide 1004b. As illustrated, the first pivot guide 1004a comprises interlocking ring pivot guide segments referred to herein as first and second matable members 1016a and 1016b that are mirror images of each other. When the matable members 1016a,b are mated, the first pivot guide 1004a defines a central aperture 1018 alignable with the central channel 606 (FIGS. 10A-10B) of the wrist 206 (FIG. 10A) and sized or otherwise configured to accommodate the flexible member 608 (FIG. 10A). Moreover, when the matable members 1016a,b are mated, protrusions extending from an end of each matable member 1016a,b axially align and help form or otherwise provide the first axle 404a for the wrist 206 (FIG. 9A). Furthermore, each matable member 1016a,b defines a radial projection 1020 alignable with a corresponding one of the cutouts 1014 (FIG. 10B) defined on the intermediate linkage 402b to help mount the first pivot guide 1004a to the distally extending lobes 1008a,b.

Figure 11A:
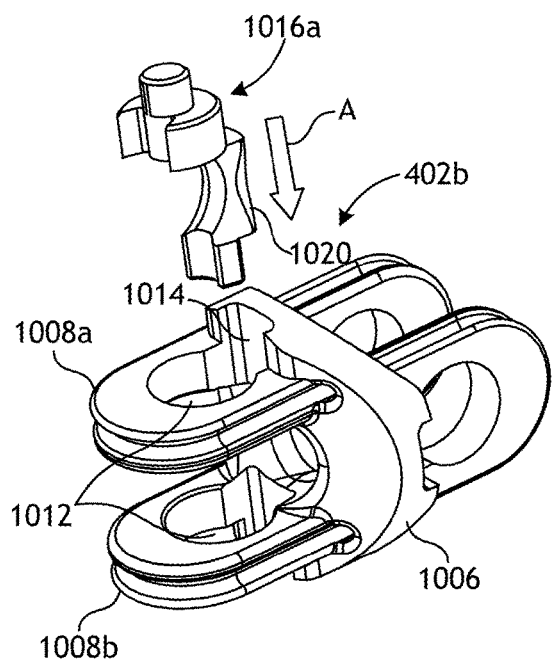
FIGS. 11A-11F depict example assembly of the first pivot guide of FIGS. 10C-10D to the intermediate linkage of FIG. 10B, according to one or more embodiments.
Figure 11B:
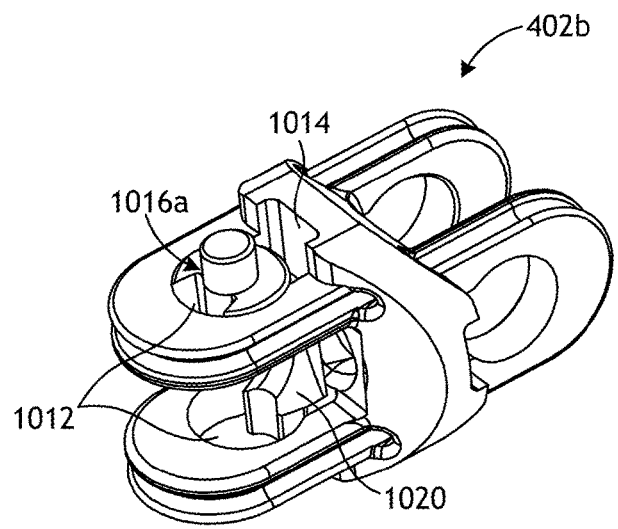
Figure 11C:
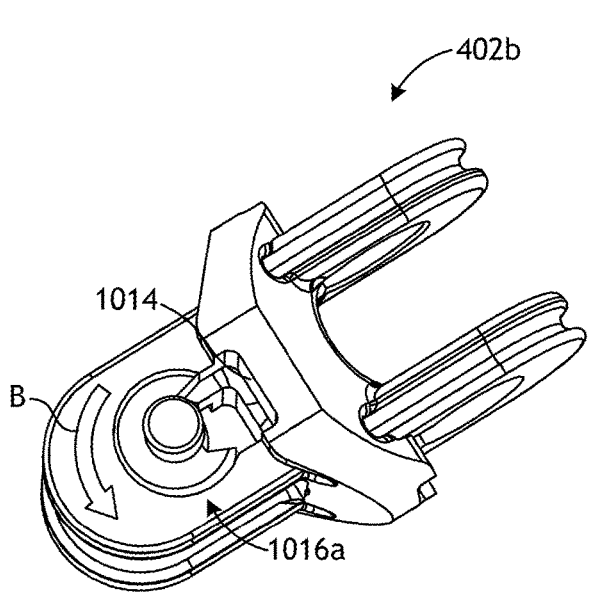

FIGS. 11A-11F depict example assembly of the first pivot guide 1004a to the intermediate linkage 402b of FIG. 10B, according to one or more embodiments. In FIG. 11A, the first matable member 1016a may be received within the apertures 1012 defined by the distally extending lobes 1008a,b. To accomplish this, the radial projection 1020 defined on the second matable member 1016b may be aligned with the cutout 1014 defined on the main body 1006 and the second matable member 1016b may then be advanced into the apertures 1012 in the direction of the arrow A. FIG. 11B shows the first matable member 1016a received within the apertures 1012 and the radial projection 1020 aligned with and received within the cutout 1014. In FIG. 11C, the first matable member 1016a is rotated 180°, as indicated by the arrow B, to move the radial projection 1020 out of the cutout 1014 in preparation for receiving the second matable member 1016b.

Figure 11D:
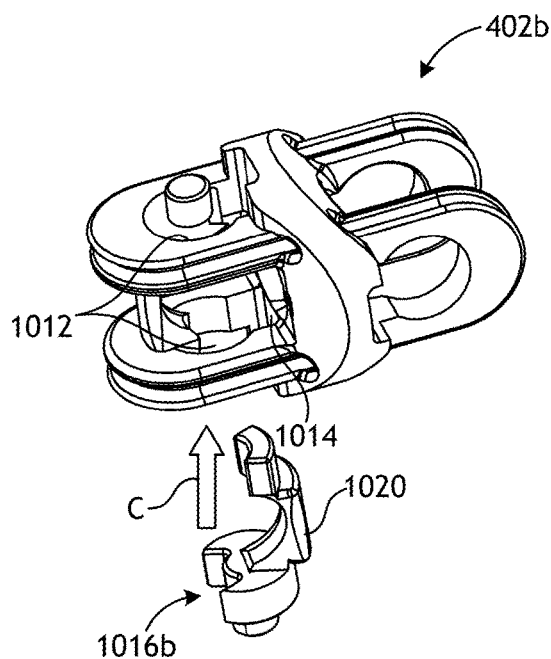
Figure 11E:
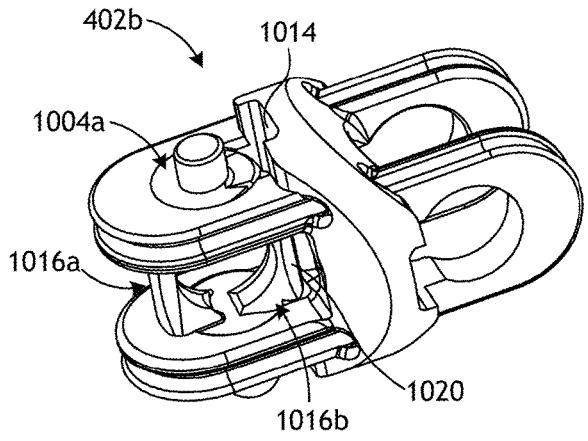
Figure 11F:
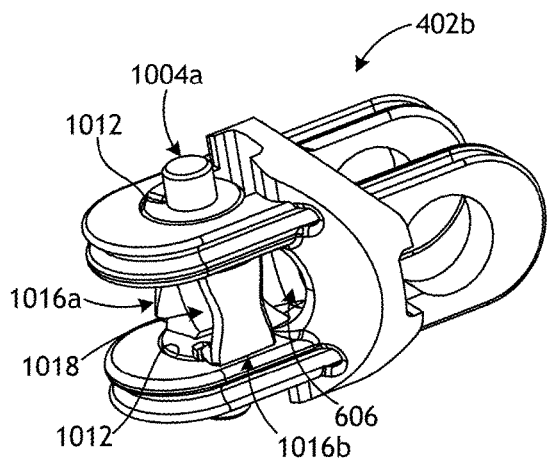

In FIG. 11D, the second matable member 1016b may be received within the apertures 1012 defined by the distally extending lobes 1008a,b by aligning the radial projection 1020 defined on the second matable member 1016b with the cutout 1014 and advancing the second matable member 1016b into the apertures 1012 in the direction of the arrow C. Advancing the second matable member 1016a into the apertures 1012 will also mate the second matable member 1016b to the first matable member 1016a. FIG. 11E shows the first and second matable members 1016a,b mated and received within the apertures 1012 to form the assembled first pivot guide 1004a. The radial projection 1020 of the second matable member 1016b is also aligned with and received within the cutout 1014. In FIG. 11F, the first pivot guide 1004a is rotated 90° to secure the first and second matable members 1016a,b within the apertures 1012 and align the central aperture 1018 with the central channel 606 of the wrist 206 (FIG. 10A) in preparation for receiving the flexible member 608 (FIG. 10A).

Referring again to FIG. 10A, example operation of the wrist 206 will now be provided, according to one or more embodiments. As illustrated, the flexible member 608 is extended through the central channel 606 of the wrist 206 and also through the central aperture 1018 of each pivot guide 1004a,b. The first and second ends 420a,b of the jaw cable 418 are shown as dashed lines extending through corresponding conduits 610 defined through the flexible member 608. The wrist 206 may be articulated in yaw motion at the first articulation joint 1002a about the first pivot axis $P_1$, and further articulated in pitch motion at the second articulation joint 1002b about the second pivot axis $P_2$. Articulating at the first and second articulation joints 1002a,b correspondingly causes the first and second pivot guides 1004a,b to rotate about the corresponding pivot axes $P_1$, $P_2$ to accommodate bending of the flexible member 608 from a straight position. The first and second pivot guides 1004a,b help to contain and support the outer diameter of the flexible member 608 at the first and second articulation joints 1002a,b and thereby prevent the flexible member 608 from flexing beyond the first and second pivot axes $P_1$, $P_2$, which will mitigate tip dive at the end effector 204 (FIG. 2).

Figure 12A:
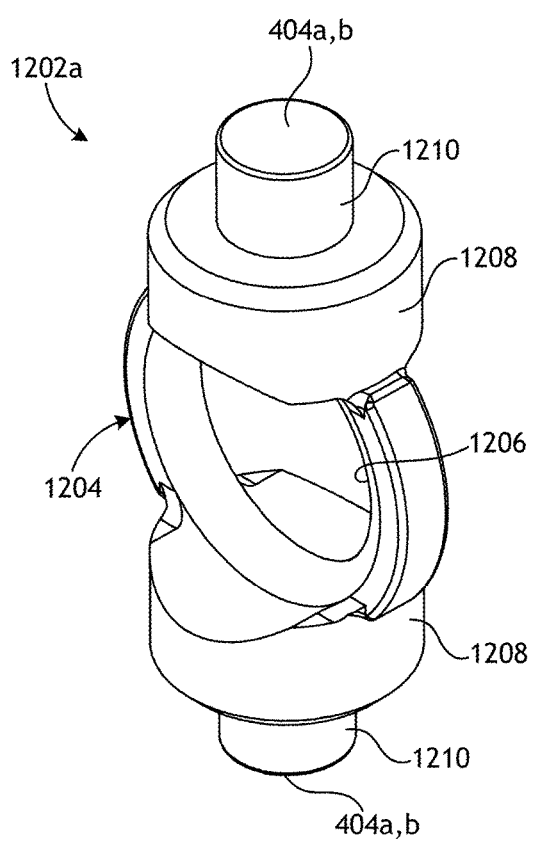
FIGS. 12A and 12B are alternate embodiments of two example pivot guides, according to one or more additional embodiments.
Figure 12B:
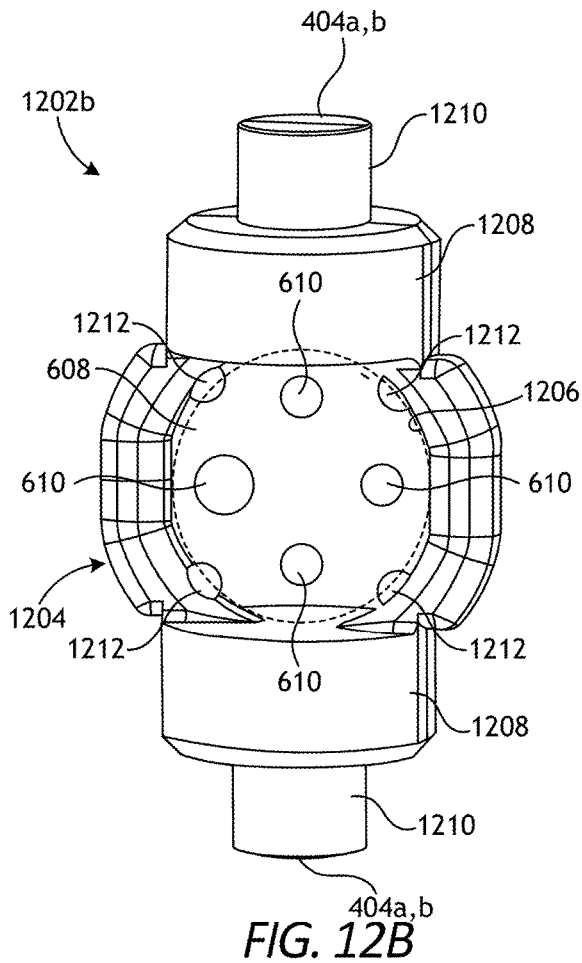

FIGS. 12A and 12B are alternate embodiments of two example pivot guides, according to one or more additional embodiments. FIG. 12A depicts a first pivot guide 1202a and FIG. 12B depicts a second pivot guide 1202b. Each pivot guide 1202a,b includes a generally annular body 1204 that defines a central aperture 1206 alignable with the central channel 606 (FIGS. 6A-6B) of the wrist 206 (FIGS. 6A-6B) and sized or otherwise configured to accommodate the flexible member 608 (FIG. 12B). Each pivot guide 1202a,b may further include opposing cylindrical heads 1208 positioned at angularly opposite sides of the annular body 1204. The cylindrical heads 1208 may be configured to be received within apertures defined on the lobes of the intermediate linkage 402b. Moreover, opposing protrusions or pins 1210 may extend radially outward from the each cylindrical head 1208 to help form or otherwise provide the first or second axles 404a,b for the wrist 206.

Referring specifically to FIG. 12B, the second pivot guide 1202b further includes one or more dimples 1212 (four shown) protruding radially inward from the annular body 1204 and into the central aperture 1206. The dimples 1212 may help secure and center the flexible member 608 within the central aperture 1206, and can create a clearance or gap between the outer diameter of the flexible member 608 and the inner diameter of the central aperture 1206. The dimples 1212 may also help to shift stress concentrations to the corners of the flexible member 608 where there is the more material and otherwise away from the location of the conduits 610 defined therethrough. Such corners of the flexible member may be characterized as "sacrificial zones". In some embodiments, as illustrated, the dimples 1212 may be angularly offset from the location of the conduits 610, which may prove advantageous in reducing stress concentrations at the conduits 610, which could extend device tool life.

Figure 13A:
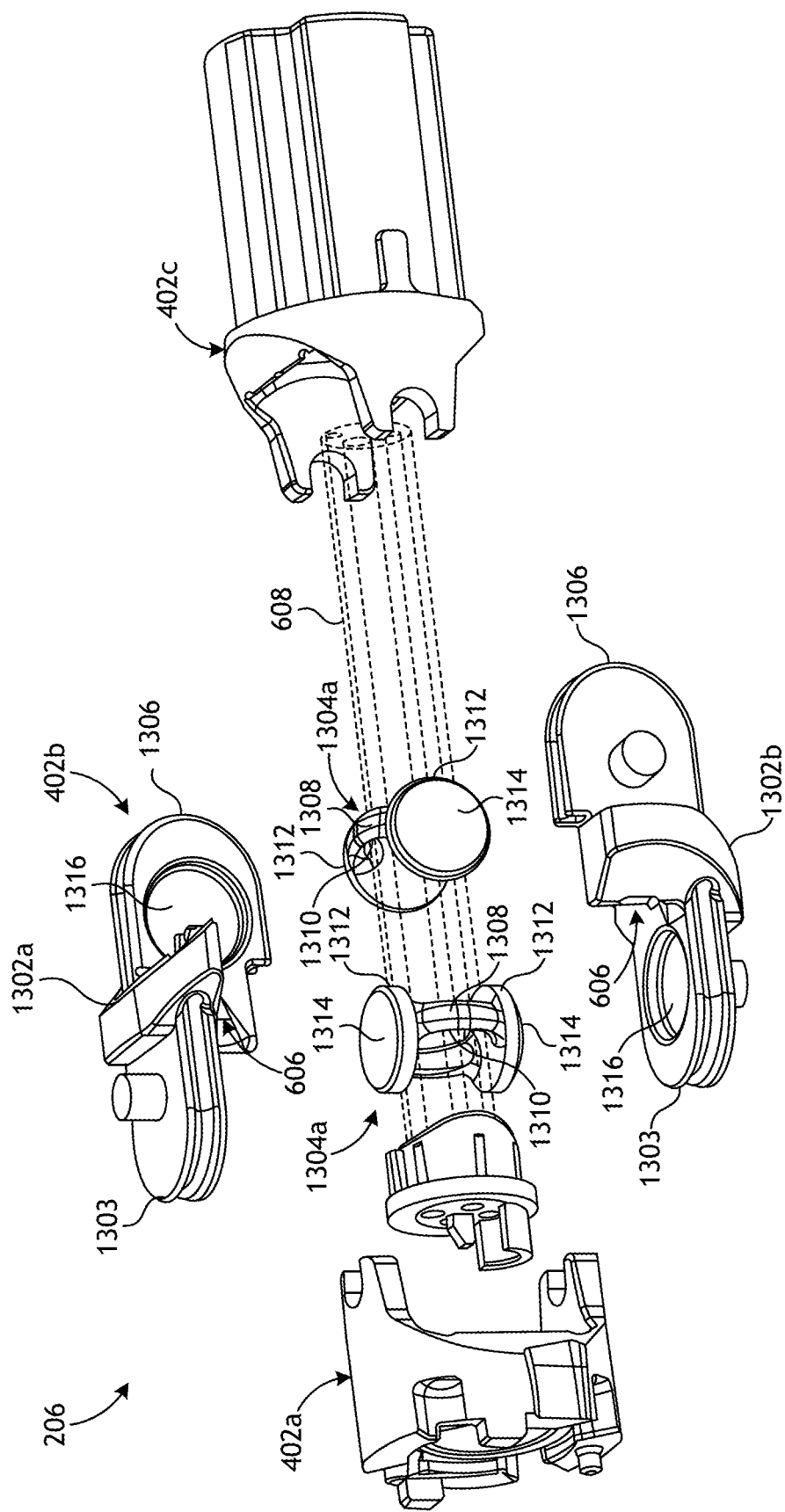
FIG. 13A is an exploded view of another example embodiment of the wrist of FIGS. 4, 5, and 6A-6B that may incorporate one or more principles of the present disclosure.

FIG. 13A is an exploded view of another example embodiment of the wrist 206, according to one or more additional embodiments. For simplicity, the drive cables 408a-d (FIGS. 4-5), the electrical conductor 422 (FIGS. 4-5), the first and second ends 420a,b of the jaw cable 418 (FIGS. 4-5), and the drive rod 430 (FIGS. 4-5) are each omitted in FIG. 8A. In the present embodiment, the intermediate linkage 402b may be made of two or more pieces or component parts, shown in the illustrated embodiment as a first intermediate part 1302a and a second intermediate part 1302b. The first and second intermediate parts 1302a,b may be identical elements or mirror images of each other and matable to form the intermediate linkage 402b and thereby help define a portion of the central channel 606 through which the flexible member 608 can extend. While only two intermediate parts 1302a,b are depicted in FIG. 13A, the intermediate linkage 402b may alternatively comprise three or more intermediate parts, without departing from the scope of the disclosure.

Each intermediate part 1302a,b may provide a distally extending lobe 1303 and a proximally extending lobe 1306 that extends orthogonal to the distally extending lobe 1303. When the intermediate parts 1302a,b are mated to form the intermediate linkage 402b, the distally extending lobes 1303 will be laterally offset from each other and the proximally extending lobes 1306 will be laterally offset from each other and angularly offset from the distally extending lobes 1306 by 900, which allows the intermediate linkage 402b to facilitate both "yaw" and "pitch" articulation of the end effector 204 (FIG. 2).

As illustrated, the wrist 206 may further include first and second pivot guides 1304a and 1304b that may be secured upon mating the first and second intermediate parts 1302a,b. Each pivot guide 1304a,b includes a generally annular body 1308 that defines a central aperture 1310 alignable with the central channel 606 of the wrist 206 and sized or otherwise configured to accommodate the flexible member 608. Internal surfaces of the central aperture 1310 may be smoothed, curved, and/or include a lubricant, which may help improve articulation joint friction and reduce galling in the surgical tool 200 (FIG. 2), thus increasing device mission life. Opposing disc-shaped heads 1312 may be positioned at angularly opposite sides of the annular body 1308 of each pivot guide 1304a,b, and each head 1312 may be configured to be received within a corresponding bearing pocket 1316 defined on an opposing lobe 1303, 1306 of the intermediate linkage 402b. The heads 1312 may be configured to rotate within the bearing pockets 1316 during operation as the flexible member 608 bends and flexes. Each head 1312 may define or otherwise provide a bearing face 1314 slidably engageable with the bottom of the adjacent bearing pocket 1316.

Figure 13B:
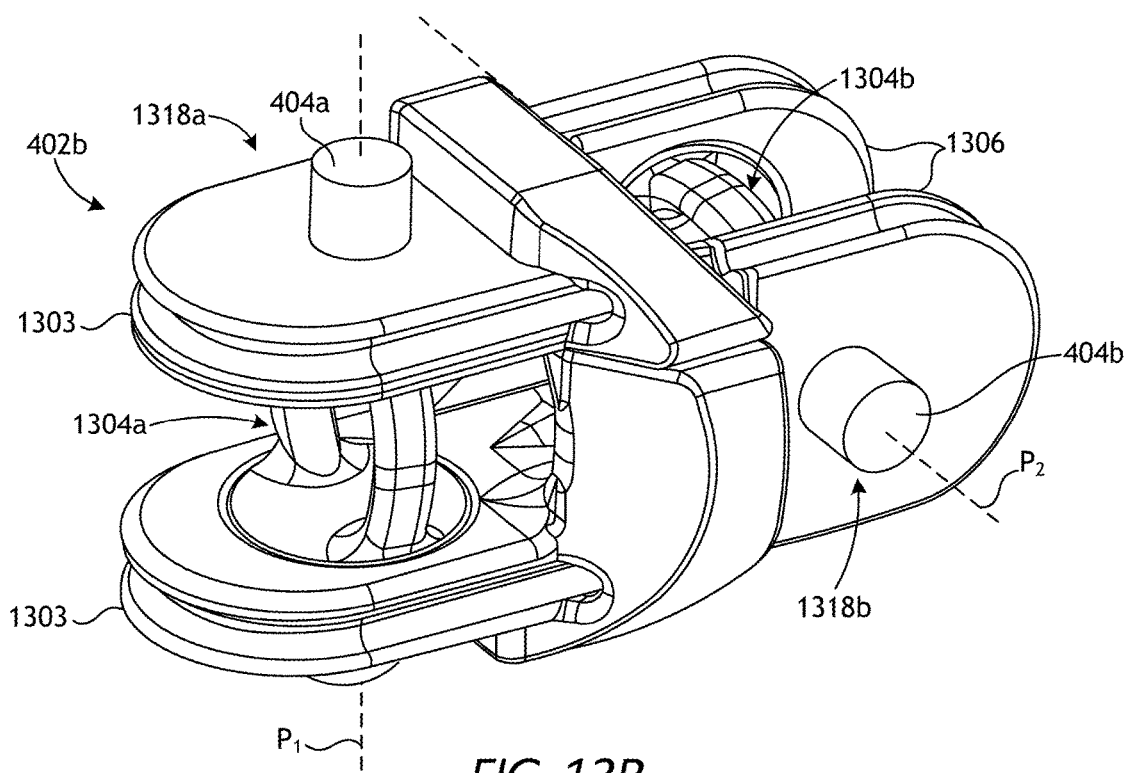
FIG. 13B is an assembled, isometric view of the intermediate linkage of FIG. 13A FIGS. 13C and 13D are cross-sectional end views of a first pivot guide.

FIG. 13B is an assembled, isometric view of the intermediate linkage 402b of FIG. 13A. As illustrated, the first axle 404a may be defined on the distally extending lobes 1303 and provide a first articulation joint 1318a, and the second axle 404b may be defined on the proximally extending lobes 1306 and provide a second articulation joint 1318b. Moreover, the first pivot axis $P_1$ extends through the first articulation joint 1318a and facilitates "yaw" movement (articulation) of the end effector 204 (FIG. 2), and the second pivot axis $P_2$ extends through the second articulation joint 1318b and facilitates "pitch" movement (articulation) of the end effector 204.

The first and second intermediate parts 1302a,b may be made of any rigid or semi-rigid material including, but not limited to, a plastic, a metal, a composite material, an elastomer, or any combination thereof. In at least one embodiment, the first and second intermediate parts 1302a,b may be made of a metal and manufactured through metal injection molding with some post machining on critical surfaces and/or pivoting locations. The first and second intermediate parts 1302a,b may be permanently or removably secured together to form the intermediate linkage 402b. Suitable securing methods include, but are not limited to, welding, an adhesive attachment, one or more mechanical fasteners, or any combination thereof. In other embodiments, securing the first and second intermediate parts 1302a,b together may not be required since once the distal and proximal linkages 402a,c (FIG. 13A) are rotatably coupled to the intermediate linkage 402b, the first and second intermediate parts 1302a,b will be trapped in place by the distal and proximal linkages 402a,c.

The first and second pivot guides 1304a,b will be secured to the intermediate linkage 402b upon mating the first and second intermediate parts 1302a,b. The first pivot guide 1304a is rotatably secured at the first articulation joint 1318a, and the second pivot guide 1304b is rotatably secured at the second articulation joint 1318b. Moreover, the pivot guides 1304a,b are rotatable about the first and second pivot axes $P_1$, $P_2$. The pivot guides 1304a,b may be made of any of the materials mentioned herein for any of the pivot guides described herein.

Figure 13C:
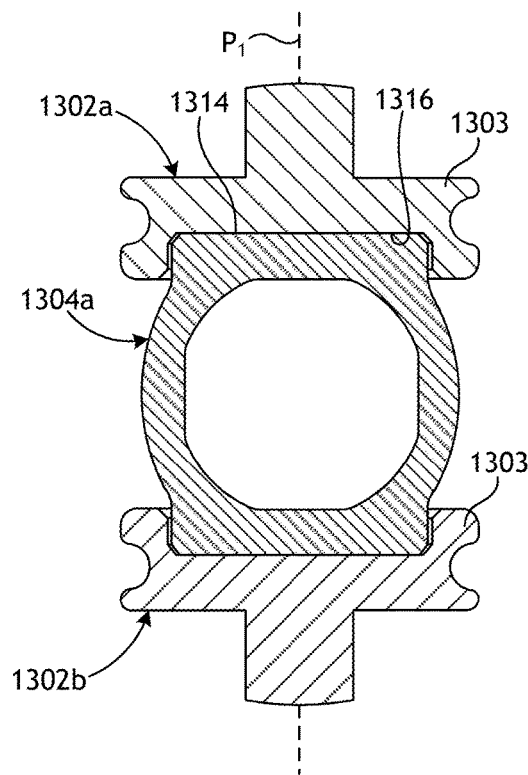
Figure 13D:
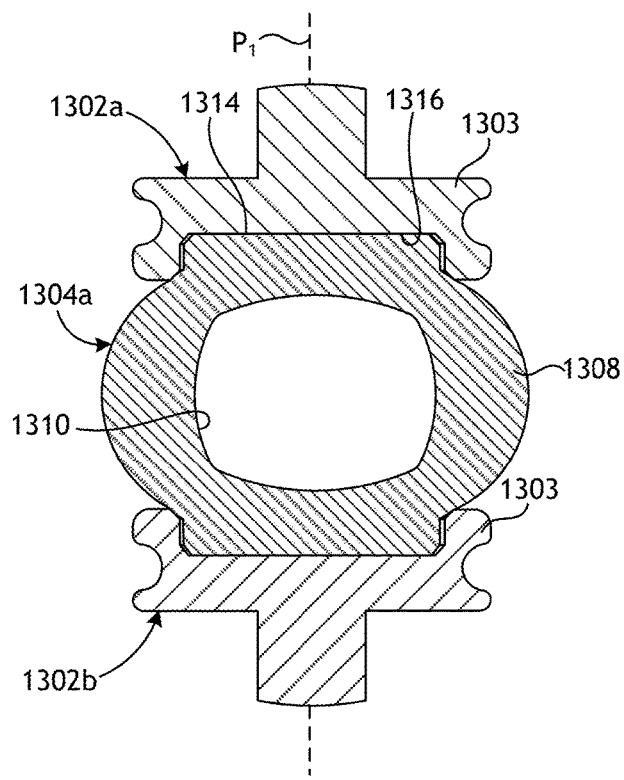

FIGS. 13C and 13D are cross-sectional end views of the first pivot guide 1304a secured between the proximally extending lobes 1303 of the first and second intermediate parts 1302a,b. As illustrated, the bearing faces 1314 are received within the corresponding bearing pockets 1316 and help the first pivot guide 1304a rotate about the first pivot axis $P_1$ as the flexible member 608 (FIG. 13A) bends and flexes during operation. In at least one embodiment, one or both of the bearing faces 1314 or the bottom of the pockets 1316 may be polished and/or include a lubricant, which may help reduce friction and galling as the pivot guide 1304a rotates during operation.

In FIG. 13D, the annular body 1308 of the first pivot guide 1304a is enlarged radially and is thicker, as compared to the embodiment of FIG. 13C. Because the first and second intermediate parts 1302a,b are matable to secure the first pivot guide 1304a, wider and larger designs of the first pivot guide 1304a can be accommodated and the first and second intermediate parts 1302a,b will be mated around the larger designs. This may prove advantageous in providing additional strength to the system. Moreover, enlarging the size of the pivot guide 1304a allows the contact radius of the central channel 1310 to also be enlarged. This will increase the radius of the arcuate surface where the elongate member 608 (and the central actuation members) contacts and bends around during articulation. Consequently, this will reduce flexure fatigue loading on the elongate member 608 and extend service life.

Figure 14:
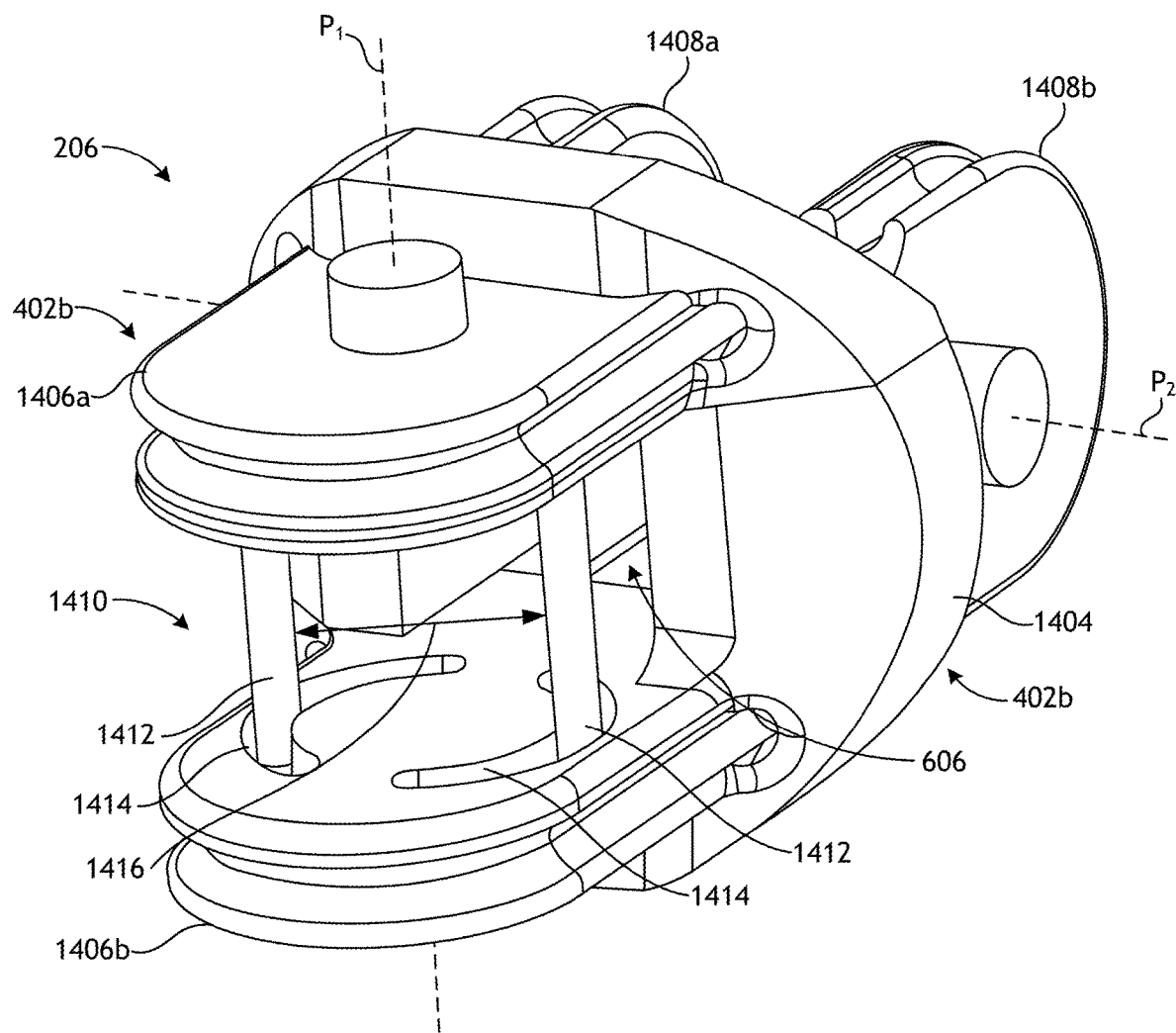
FIG. 14 is an isometric side view of another example embodiment of a portion of the wrist of FIGS. 4, 5, and 6A-6B that may incorporate one or more principles of the present disclosure.

FIG. 14 is an isometric side view of another example embodiment of a portion of the wrist 206 that may incorporate one or more principles of the present disclosure. In the illustrated view, the distal and proximal linkages 402a,c (FIGS. 4-5) and the flexible member 608 (FIGS. 6A-6B and 7A-7B) are omitted for simplicity, and the flexible member 608 would otherwise extend through the central channel 606 partially defined by the intermediate linkage 402b. The first pivot axis $P_1$ extends through a first articulation joint 1402a and facilitates "yaw" movement (articulation) of the end effector 204 (FIG. 2), and the second pivot axis $P_2$ extends through a second articulation joint 1402b and facilitates "pitch" movement (articulation) of the end effector 204.

As illustrated, the intermediate linkage 402b includes a main body 1404 that defines a portion of the central channel 606 and is made up of two parts or pieces, similar to the first and second intermediate parts 1302a,b of FIGS. 13A-13B. A pair of distally extending lobes 1406a and 1406b extend distally from the body 1404 and are laterally offset from each other, and a pair of proximally extending lobes 1408a and 1408b extend proximally from the body 1404 and are laterally offset from each other. The proximally extending lobes 1408a,b are angularly offset from the distally extending lobes 1406a,b by 90°, which allows the intermediate linkage 402b to facilitate both "yaw" and "pitch" articulation of the end effector 204 (FIG. 2).

In the illustrated embodiment, each pair of opposing lobes 1406a,b and 1408a,b may be configured to secure a pivot guide 1410 therebetween to help support the flexible member 608 (FIGS. 6A-6B and 7A-7B) during articulation. Only the pivot guide 1410 positioned at the distally extending lobes 1406a,b is visible in FIG. 14, but the structure and operation of each pivot guide 1410 may be substantially similar. As illustrated, the pivot guide 1410 may comprise one or more pins 1412 received within and extending between corresponding arcuate grooves or slots 1414 defined in the opposing lobes 1406a,b. In the illustrated embodiment, two arcuate slots 1414 are defined in the opposing lobes 1406a,b, but a single arcuate or annular slot could be defined in the opposing lobes 1406a,b, without departing from the scope of the disclosure. Moreover, in the illustrated embodiment, a single pin 1412 is received within the corresponding arcuate slots 1414, but more than one pin 1412 may alternatively be received within the corresponding arcuate slots 1414, without departing from the scope of the disclosure.

The pins 1412 may be angularly offset from each other to define a gap or central aperture 1416 alignable with the central channel 606 and sized or otherwise configured to accommodate the flexible member 608 (FIGS. 6A-6B and 7A-7B) therethrough. The pins 1412 may be able to translate within the corresponding slot(s) 1414 during operation as the flexible member 608 bends and flexes, and thereby help to prevent the flexible member 608 from dipping below the pivot axes $P_1$, $P_2$, which helps mitigate or prevent tip dive.

Embodiments disclosed herein include:

A. An articulable wrist for an end effector that includes a first linkage, a second linkage rotatably coupled to the first linkage at a first articulation joint, a flexible member extending at least partially through a central channel cooperatively defined by the first and second linkages, and a first pivot guide rotatably coupled to the second linkage at the first articulation joint and rotatable about a first pivot axis extending through the first articulation joint, the first pivot guide defining a central aperture alignable with the central channel and sized to accommodate the flexible member therethrough, wherein the first pivot guide supports an outer diameter of the flexible member at the first articulation joint and thereby prevents the flexible member from flexing beyond the first pivot axis during articulation.

B. A surgical tool that includes a drive housing, an elongate shaft that extends from the drive housing, an end effector arranged at an end of the elongate shaft, an articulable wrist that interposes the end effector and the elongate shaft, the articulable wrist including a first linkage, a second linkage rotatably coupled to the first linkage at a first articulation joint, a flexible member extending at least partially through a central channel cooperatively defined by the first and second linkages, and a first pivot guide rotatably coupled to the second linkage at the first articulation joint and rotatable about a first pivot axis extending through the first articulation joint, the first pivot guide defining a central aperture alignable with the central channel and sized to accommodate the flexible member therethrough, wherein the first pivot guide supports an outer diameter of the flexible member at the first articulation joint and thereby prevents the flexible member from flexing beyond the first pivot axis during articulation.

C. A method of operating a surgical tool including positioning the surgical tool adjacent a patient for operation, the surgical tool including a drive housing, an elongate shaft that extends from the drive housing, an end effector arranged at an end of the elongate shaft, and a wrist that interposes the end effector and the elongate shaft and includes a first linkage, a second linkage rotatably coupled to the first linkage at a first articulation joint, a flexible member extending at least partially through a central channel cooperatively defined by the first and second linkages, and a first pivot guide rotatably coupled to the second linkage at the first articulation joint and rotatable about a first pivot axis extending through the first articulation joint, the first pivot guide defining a central aperture alignable with the central channel and sized to accommodate the flexible member therethrough. The method further including articulating the wrist and simultaneously bending the flexible member within the central channel, and supporting an outer diameter of the flexible member at the first articulation joint with the first pivot guide and thereby preventing the flexible member from flexing beyond the first pivot axis during articulation.

Each of embodiments A, B, and C may have one or more of the following additional elements in any combination: Element 1: further comprising an axially-extending conduit defined in the flexible member to receive a closure cable used to actuate jaws of the end effector, wherein the pivot guide supports the outer diameter of the flexible member at the first articulation joint and prevents a centerline of the closure cable from deviating below the first pivot axis during clamping. Element 2: wherein the second linkage comprises a main body that defines a portion of the central channel, a pair of lobes extending from the main body and laterally offset from each other, and an aperture defined in each lobe and sized to rotatably receive a portion of the first pivot guide. Element 3: wherein the first pivot guide comprises a cylindrical body that defines the central aperture and has first and second ends rotatably received into the aperture defined on each lobe, and a protrusion extending outward from each of the first and second ends and providing a first axle extending along the first pivot axis, wherein the first linkage is rotatably coupled to the second linkage at the first axle. Element 4: wherein the first pivot guide comprises an annular body that defines the central aperture, and opposing pins extending radially outward from the annular body at angularly opposite sides of the annular body, wherein the opposing pins are rotatably received into the aperture defined on each lobe. Element 5: wherein the first pivot guide comprises first and second matable members that cooperatively define the central aperture when mated, a protrusion extending from an end of each matable member and providing a first axle extending along the first pivot axis, wherein the first linkage is rotatably coupled to the second linkage at the first axle. Element 6: wherein the first pivot guide comprises an annular body that defines the central aperture, opposing cylindrical heads positioned at angularly opposite sides of the annular body and rotatably received into the aperture defined on each lobe, and opposing pins extending radially outward from the each cylindrical head and providing a first axle extending along the first pivot axis, wherein the first linkage is rotatably coupled to the second linkage at the first axle. Element 7: further comprising one or more dimples protruding radially inward from the annular body and into the central aperture. Element 8: wherein the second linkage comprises a first intermediate part providing a first lobe, and a second intermediate part providing a second lobe laterally offset from the first lobe when the first and second intermediate parts are mated to form the second linkage and define the central channel. Element 9: wherein the first pivot guide comprises an annular body that defines the central aperture, and opposing disc-shaped heads positioned at angularly opposite sides of the annular body and rotatably receivable within a bearing pocket defined on a corresponding one of the first or second lobes, wherein mating the first and second intermediate parts secures the first pivot guide to the articulable wrist. Element 10: wherein the second linkage comprises a main body that defines a portion of the central channel, a pair of lobes extending from the main body and laterally offset from each other, and one or more arcuate slots defined in each lobe, and wherein the first pivot guide comprises two or more pins received within and extending between the one or more arcuate slots defined in each lobe, wherein the two or more pins are angularly offset from each other to define the central aperture. Element 11: further comprising a third linkage rotatably coupled to the second linkage at a second articulation joint and cooperatively defining the central channel with the first and second linkages, and a second pivot guide rotatably coupled to the second linkage at the second articulation joint and rotatable about a second pivot axis extending through the second articulation joint, the second pivot guide defining a central aperture alignable with the central channel and sized to accommodate the flexible member therethrough, wherein the second pivot guide supports the outer diameter of the flexible member at the second articulation joint and prevents the flexible member from flexing beyond the second pivot axis during articulation. Element 12: wherein the second linkage comprises a main body that defines a portion of the central channel, a pair distally extending lobes extending distally from the main body and laterally offset from each other, a pair proximally extending lobes extending proximally from the main body and laterally offset from each other, wherein the pair of proximally extending lobes are angularly offset from the pair of distally extending lobes by 90°, an aperture defined in each distally extending lobe and sized to rotatably receive a portion of the first pivot guide, and an aperture defined in each proximally extending lobe and sized to rotatably receive a portion of the second pivot guide. Element 13: wherein the first pivot guide is made of a material selected from the group consisting of an electrically-conductive material, a non-conductive material, a plastic, a metal, a composite material, an elastomer, and any combination thereof.

Element 14: wherein the end effector includes jaws actuatable to open and close, the surgical tool further comprising a closure cable extending from the drive housing to the end effector and actuatable to close the jaws, wherein the closure cable extends through an axially-extending conduit defined in the flexible member, and wherein the pivot guide supports the outer diameter of the flexible member at the first articulation joint and prevents a centerline of the closure cable from deviating below the first pivot axis during closing. Element 15: wherein the second linkage comprises a main body that defines a portion of the central channel, a pair of lobes extending from the main body and laterally offset from each other, and an aperture defined in each lobe and sized to rotatably receive a portion of the first pivot guide. Element 16: wherein the first pivot guide comprises first and second matable members that cooperatively define the central aperture when mated, a protrusion extending from an end of each matable member and providing a first axle extending along the first pivot axis, wherein the first linkage is rotatably coupled to the second linkage at the first axle. Element 17: wherein the first pivot guide comprises an annular body that defines the central aperture, and one or more dimples protruding radially inward from the annular body and into the central aperture. Element 18: wherein the second linkage comprises a first intermediate part providing a first lobe, and a second intermediate part providing a second lobe laterally offset from the first lobe when the first and second intermediate parts are mated to form the second linkage and define the central channel, and wherein the first pivot guide comprises an annular body that defines the central aperture, and opposing disc-shaped heads positioned at angularly opposite sides of the annular body and rotatably receivable within a bearing pocket defined on a corresponding one of the first or second lobes.

Element 19: wherein the wrist further includes a third linkage rotatably coupled to the second linkage at a second articulation joint and cooperatively defining the central channel with the first and second linkages, and a second pivot guide rotatably coupled to the second linkage at the second articulation joint and rotatable about a second pivot axis extending through the second articulation joint, the second pivot guide defining a central aperture alignable with the central channel and sized to accommodate the flexible member therethrough, the method further comprising actuating a closure cable extending from the drive housing to the end effector to close jaws of the end effector, wherein the closure cable extends through a first axially-extending conduit defined in the flexible member; supporting the outer diameter of the flexible member at the first articulation joint with the pivot guide and thereby preventing a centerline of the closure cable from deviating below the first pivot axis during closing; actuating an open cable extending from the drive housing to the end effector to open the jaws, wherein the open cable extends through a second axially-extending conduit defined in the flexible member angularly offset from the first axially-extending conduit by 90°, and supporting the outer diameter of the flexible member at the second articulation joint with the second pivot guide and thereby preventing a centerline of the open cable from deviating across the second pivot axis during opening.

By way of non-limiting example, exemplary combinations applicable to A, B, and C include: Element 2 with Element 3; Element 3 with Element 4; Element 3 with Element 5; Element 3 with Element 6; Element 6 with Element 7; Element 8 with Element 9; Element 11 with Element 12; Element 15 with Element 16; and Element 16 with Element 17.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. An articulable wrist for an end effector, comprising:
   a first linkage providing a body and a pair of lobes extending from the body and laterally offset from each other;
   a pivot guide defining a central aperture and providing opposing cylindrical heads rotatably received into corresponding apertures defined in each lobe, the pivot guide further including opposing pins extending radially outward from each cylindrical head;
   a second linkage rotatably coupled to the first linkage at the opposing pins and thereby defining an articulation joint articulable about a pivot axis; and
   a flexible member extending through the central aperture and a central channel cooperatively defined by the first and second linkages,
   wherein the pivot guide supports an outer diameter of the flexible member at the articulation joint and thereby prevents the flexible member from flexing beyond the pivot axis during articulation.

2. The articulable wrist of claim 1, further comprising an axially-extending conduit defined in the flexible member to receive a closure cable used to actuate jaws of the end effector, wherein the pivot guide supports the outer diameter of the flexible member at the articulation joint and prevents a centerline of the closure cable from deviating below the pivot axis during clamping of the jaws.

3. The articulable wrist of claim 1, wherein the opposing pins provide an axle extending along the pivot axis.

4. The articulable wrist of claim 1, wherein the pivot guide comprises a cylindrical body that defines the central aperture and provides the opposing cylindrical heads on opposite sides of the cylindrical body.

5. The articulable wrist of claim 1, wherein the pivot guide comprises an annular body that defines the central aperture and the opposing pins are provided on angularly opposite sides of the annular body.

6. The articulable wrist of claim 1, wherein the pivot guide comprises first and second matable members that cooperatively define the central aperture when mated.

7. The articulable wrist of claim 6, wherein cutouts are defined on opposing sides of the body of the first linkage and contiguous with the apertures defined in the corresponding lobes, and wherein each matable member provides a radial projection alignable with a corresponding one of the cutouts to mount the pivot guide to the corresponding lobes.

8. The articulable wrist of claim 1, further comprising one or more dimples protruding radially inward into the central aperture.

9. The articulable wrist of claim 1, wherein the first linkage comprises:
 a first intermediate part providing a first lobe of the pair of lobes; and
 a second intermediate part providing a second lobe of the pair of lobes and laterally offset from the first lobe when the first and second intermediate parts are mated to form the first linkage.

10. The articulable wrist of claim 1, wherein the pivot guide is a first pivot guide, the articulation axis is a first articulation axis, the pivot axis is a first pivot axis, and the pair of lobes comprise a pair of proximally extending lobes, the articulable wrist further comprising:
 a pair of distally extending lobes extending distally from the body and laterally offset from each other, the pair of distally extending lobes being angularly offset from the pair of proximally extending lobes by 90°;
 a second pivot guide defining a central aperture and providing opposing cylindrical heads rotatably received into corresponding apertures defined in each lobe of the pair of lobes extending distally from the body, the second pivot guide further including opposing pins extending radially outward from each cylindrical head of the second pivot guide;
 a third linkage rotatably coupled to the first linkage at the opposing pins of the second pivot guide and thereby defining a second articulation joint articulable about a second pivot axis orthogonal to the first pivot axis;
 wherein the second pivot guide supports the outer diameter of the flexible member at the second articulation joint and prevents the flexible member from flexing beyond the second pivot axis during articulation.

11. The articulable wrist of claim 1, wherein the pivot guide is made of a material selected from the group consisting of an electrically-conductive material, a non-conductive material, a plastic, a metal, a composite material, an elastomer, and any combination thereof.

12. A surgical tool, comprising:
 an elongate shaft extending from a drive housing;
 an end effector arranged at an end of the elongate shaft;
 an articulable wrist interposing the end effector and the elongate shaft and including:
  a first linkage providing a body and a pair of lobes extending from the body and laterally offset from each other;
  a pivot guide defining a central aperture and providing opposing cylindrical heads rotatably received into corresponding apertures defined in each lobe, the pivot guide further including opposing pins extending radially outward from each cylindrical head;
  a second linkage rotatably coupled to the first linkage at the opposing pins and thereby defining an articulation joint articulable about a pivot axis; and
  a flexible member extending through the central aperture and a central channel cooperatively defined by the first and second linkages,
 wherein the pivot guide supports an outer diameter of the flexible member at the articulation joint and thereby prevents the flexible member from flexing beyond the pivot axis during articulation.

13. The surgical tool of claim 12, wherein the end effector includes jaws actuatable to open and close, the surgical tool further comprising:
 a closure cable extending from the drive housing to the end effector and actuatable to close the jaws, wherein the closure cable extends through an axially-extending conduit defined in the flexible member, and
 wherein the pivot guide supports the outer diameter of the flexible member at the articulation joint and prevents a centerline of the closure cable from deviating below the pivot axis during closing.

14. The surgical tool of claim 12, wherein the pivot guide comprises a cylindrical body that defines the central aperture and provides the opposing cylindrical heads on opposite sides of the cylindrical body.

15. The surgical tool of claim 12, wherein the pivot guide comprises first and second matable members that cooperatively define the central aperture when mated.

16. The surgical tool of claim 12, further comprising one or more dimples protruding radially inward into the central aperture.

17. The surgical tool of claim 1, wherein the first linkage comprises:
 a first intermediate part providing a first lobe of the pair of lobes; and
 a second intermediate part providing a second lobe of the pair of lobes and laterally offset from the first lobe when the first and second intermediate parts are mated to form the first linkage.

18. The surgical tool of claim 1, wherein the pivot guide is a first pivot guide, the articulation axis is a first articulation axis, the pivot axis is a first pivot axis, and the pair of lobes comprise a pair of proximally extending lobes, the articulable wrist further comprising:
 a pair of distally extending lobes extending distally from the body and laterally offset from each other, the pair of distally extending lobes being angularly offset from the pair of proximally extending lobes by 90°;
 a second pivot guide defining a central aperture and providing opposing cylindrical heads rotatably received into corresponding apertures defined in each lobe of the pair distally extending lobes, the second pivot guide further including opposing pins extending radially outward from each cylindrical head of the second pivot guide;
 a third linkage rotatably coupled to the first linkage at the opposing pins of the second pivot guide and thereby defining a second articulation joint articulable about a second pivot axis orthogonal to the first pivot axis;

wherein the second pivot guide supports the outer diameter of the flexible member at the second articulation joint and prevents the flexible member from flexing beyond the second pivot axis during articulation.

19. A method of operating a surgical tool, comprising:

positioning the surgical tool adjacent a patient for operation, the surgical tool including a drive housing, an elongate shaft that extends from the drive housing, an end effector arranged at an end of the elongate shaft, and a wrist that interposes the end effector and the elongate shaft and includes:

- a first linkage providing a body and a pair of lobes extending from the body and laterally offset from each other;
- a first pivot guide defining a central aperture and providing opposing cylindrical heads rotatably received into corresponding apertures defined in each lobe, the first pivot guide further including opposing pins extending radially outward from each cylindrical head;
- a second linkage rotatably coupled to the first linkage at the opposing pins and thereby defining a first articulation joint articulable about a first pivot axis; and
- a flexible member extending through the central aperture and a central channel cooperatively defined by the first and second linkages;

articulating the wrist and simultaneously bending the flexible member within the central channel; and supporting an outer diameter of the flexible member at the first articulation joint with the first pivot guide and thereby preventing the flexible member from flexing beyond the first pivot axis during articulation.

20. The method of claim 19, wherein the pair of lobes comprise a pair of proximally extending lobes and the wrist further includes:

a pair distally extending lobes extending distally from the body and laterally offset from each other, the pair of distally extending lobes being angularly offset from the pair of proximally extending lobes by 90°;

a second pivot guide defining a central aperture and providing opposing cylindrical heads rotatably received into corresponding apertures defined in each lobe of the pair of distally extending lobes, the second pivot guide further including opposing pins extending radially outward from each cylindrical head of the second pivot guide;

a third linkage rotatably coupled to the first linkage at the opposing pins of the second pivot guide and thereby defining a second articulation joint articulable about a second pivot axis orthogonal to the first pivot axis, the method further comprising:

actuating a closure cable extending from the drive housing to the end effector to close jaws of the end effector, wherein the closure cable extends through a first axially-extending conduit defined in the flexible member;

supporting the outer diameter of the flexible member at the first articulation joint with the first pivot guide and thereby preventing a centerline of the closure cable from deviating below the first pivot axis during closing;

actuating an open cable extending from the drive housing to the end effector to open the jaws, wherein the open cable extends through a second axially-extending conduit defined in the flexible member angularly offset from the first axially-extending conduit by 90°; and supporting the outer diameter of the flexible member at the second articulation joint with the second pivot guide and thereby preventing a centerline of the open cable from deviating across the second pivot axis during opening.

* * * * *